United States Patent
Gardner, Jr. et al.

(10) Patent No.: US 7,057,721 B2
(45) Date of Patent: Jun. 6, 2006

(54) WIDE FIELD METHOD FOR DETECTING PATHOGENIC MICROORGANISMS

(75) Inventors: Charles W. Gardner, Jr., Gibsonia, PA (US); John S. Maier, Pittsburgh, PA (US); Matthew P. Nelson, Pittsburgh, PA (US); Robert C. Schweitzer, Pittsburgh, PA (US); Patrick J. Treado, Pittsburgh, PA (US); G. Steven Vanni, Pittsburgh, PA (US); Julianne Wolfe, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 297 days.

(21) Appl. No.: 10/608,470

(22) Filed: Jun. 27, 2003

(65) Prior Publication Data
US 2005/0185178 A1    Aug. 25, 2005

Related U.S. Application Data

(63) Continuation-in-part of application No. 10/339,807, filed on Jan. 10, 2003, now Pat. No. 6,765,668.

(60) Provisional application No. 60/347,806, filed on Jan. 10, 2002.

(51) Int. Cl.
*G01J 3/44*     (2006.01)
*G01N 21/65*    (2006.01)

(52) U.S. Cl. .................................... 356/301

(58) Field of Classification Search ................ 356/301
See application file for complete search history.

(56) References Cited

U.S. PATENT DOCUMENTS

| | | | |
|---|---|---|---|
| 4,847,198 A | 7/1989 | Nelson et al. | |
| 5,255,067 A | 10/1993 | Carrabba et al. | |
| 5,256,532 A | 10/1993 | Melnicoff et al. | |
| 5,266,498 A | 11/1993 | Tarcha et al. | |
| 5,306,403 A | 4/1994 | Vo-Dinh | |
| 5,334,509 A | 8/1994 | Riordan | |
| 5,376,556 A | 12/1994 | Tarcha et al. | |
| 5,400,136 A | 3/1995 | Vo-Dinh | |
| 5,496,700 A | 3/1996 | Ligler et al. | |
| 5,543,329 A | 8/1996 | Bedell | |
| 5,637,458 A | 6/1997 | Frankel et al. | |
| 5,814,516 A | 9/1998 | Vo-Dinh | |
| 5,821,066 A | 10/1998 | Pyle et al. | |
| 5,866,430 A | 2/1999 | Grow | |
| 5,895,922 A | 4/1999 | Ho | |
| 5,938,617 A | 8/1999 | Vo-Dinh | |
| 6,040,191 A | 3/2000 | Grow | |

(Continued)

OTHER PUBLICATIONS

Petrich, Wolfgang, "Mid-Infrared and Raman Spectroscopy for Medical Diagnostics", Applied Spectroscopy Reviews, 2001, 36(2&3), pp. 181-237.

(Continued)

*Primary Examiner*—F. L. Evans
(74) *Attorney, Agent, or Firm*—Duane Morris LLP

(57) ABSTRACT

Pathogenic microorganisms are detected in a wide field of view and classified by Raman light scattered light from these organisms together with digital pattern recognition of their spectral patterns.

45 Claims, 43 Drawing Sheets

U.S. PATENT DOCUMENTS

| | | |
|---|---|---|
| 6,040,906 A | 3/2000 | Harhay |
| 6,087,182 A | 7/2000 | Jeng et al. |
| 6,259,524 B1 | 7/2001 | Hofstraat et al. |
| 6,261,848 B1 | 7/2001 | Anderson et al. |
| 6,313,423 B1 | 11/2001 | Sommer et al. |
| 6,316,197 B1 | 11/2001 | Das et al. |
| 6,483,581 B1 | 11/2002 | Ben-Amotz et al. |
| 2002/0132371 A1 | 9/2002 | Kreimer et al. |
| 2002/0151041 A1 | 10/2002 | Kreimer et al. |
| 2003/0073139 A1 | 4/2003 | Kreimer et al. |

OTHER PUBLICATIONS

Naumann, Dieter, "FT-Infrared and FT-Raman Spectroscopy in Biomedical Research", Applied Spectroscopy Reviews, 2001, 36(2&3), pp. 239-298.

FIG. 1

*The Integrated Detector Sample Cell*

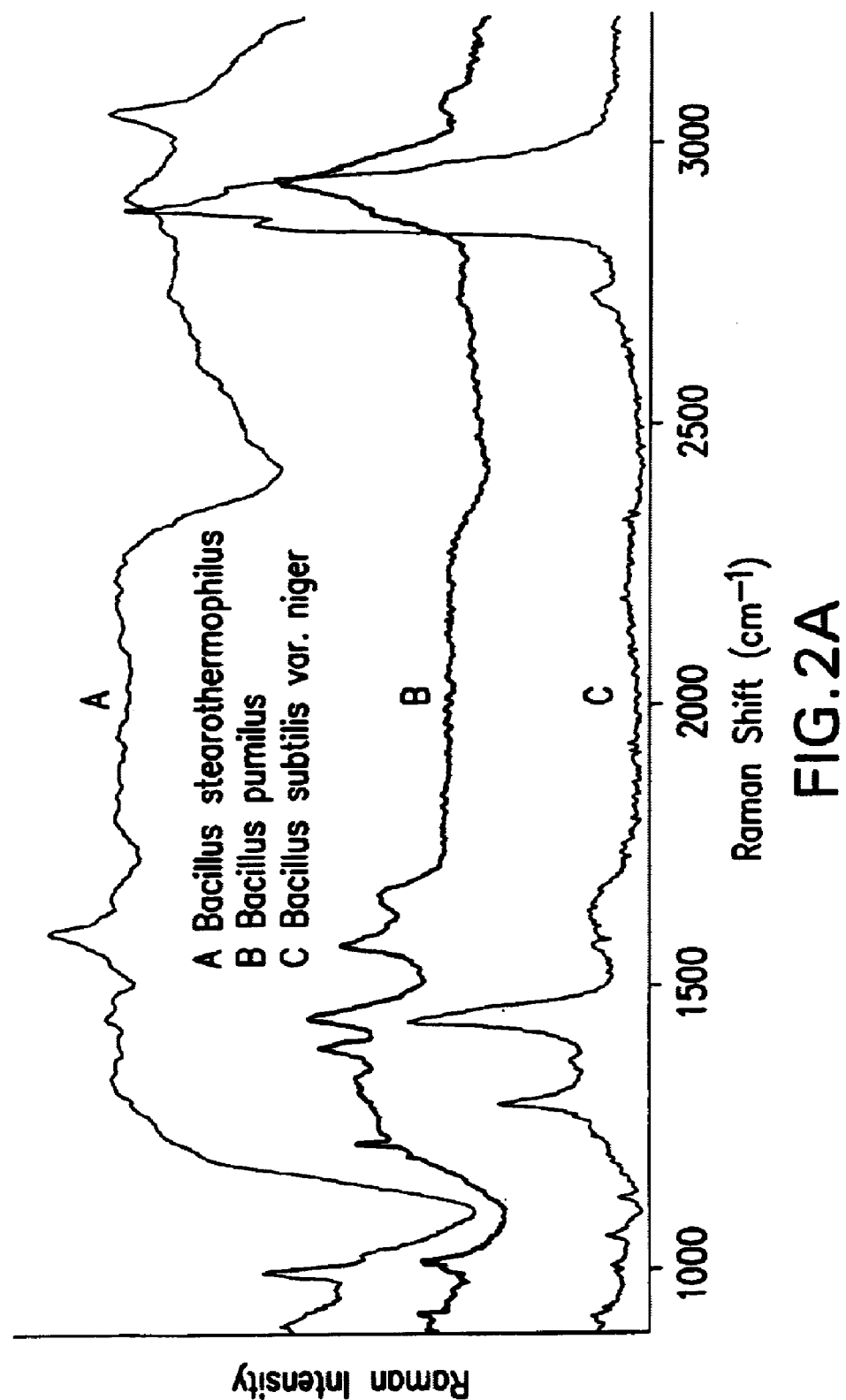

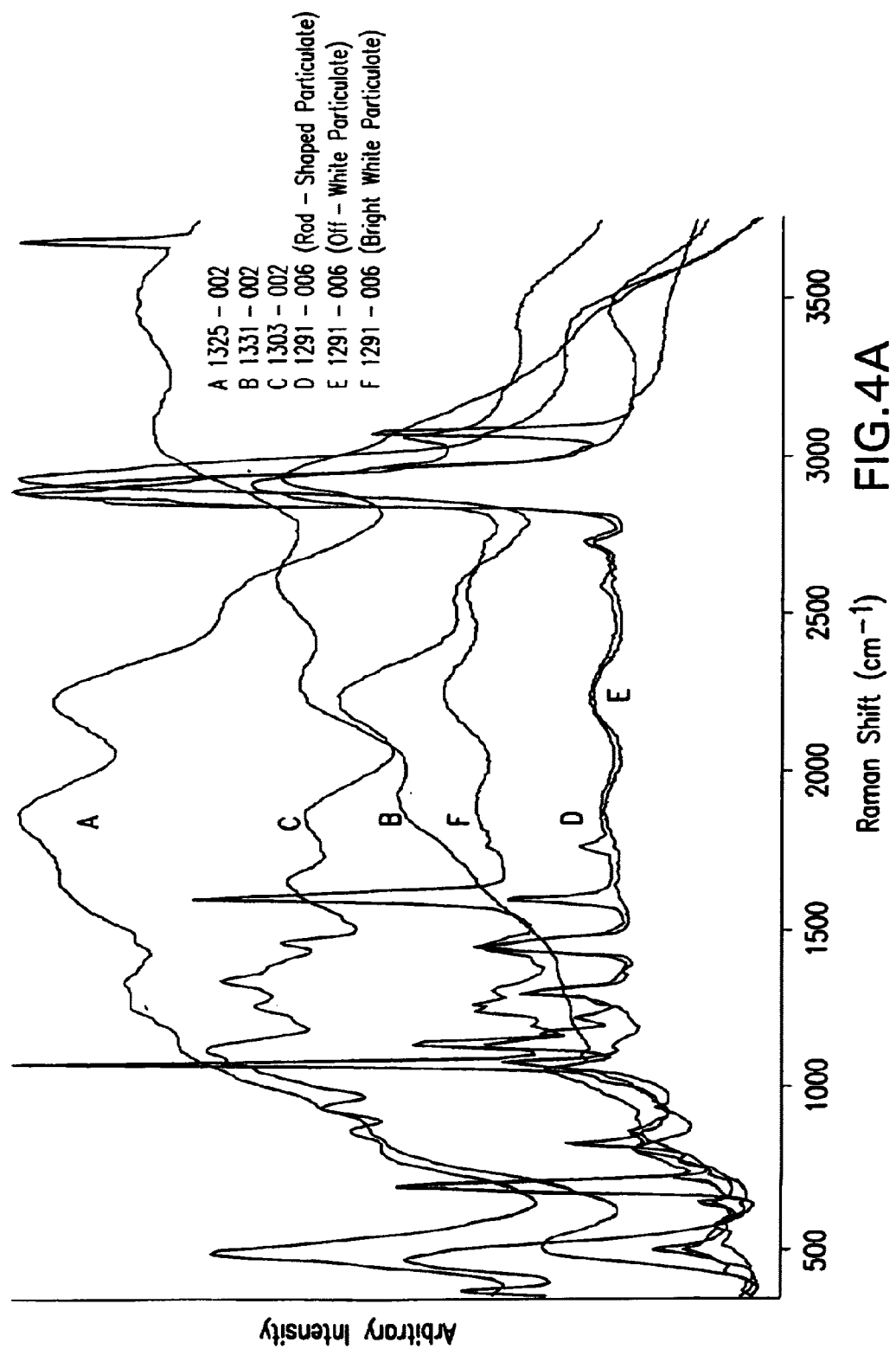

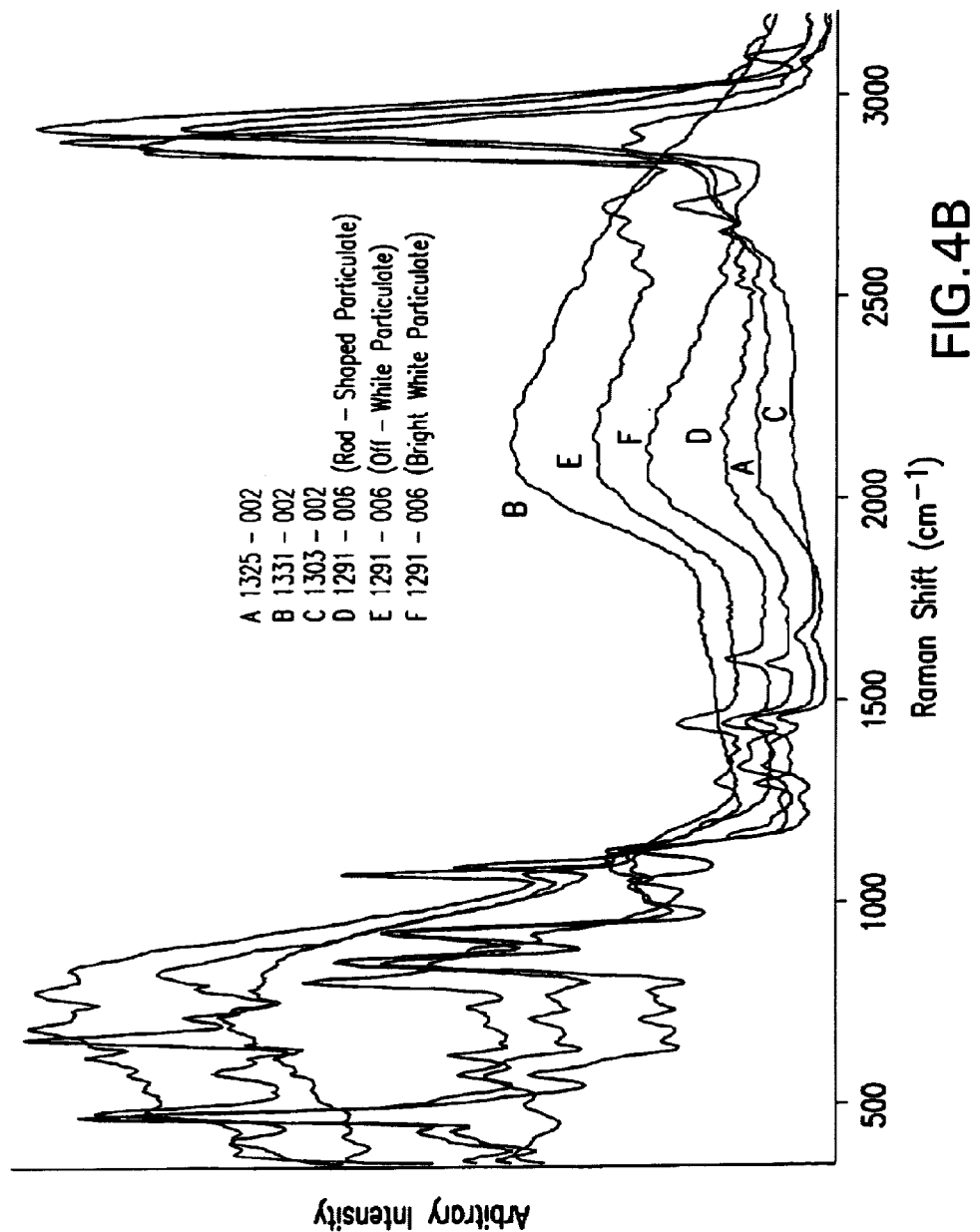

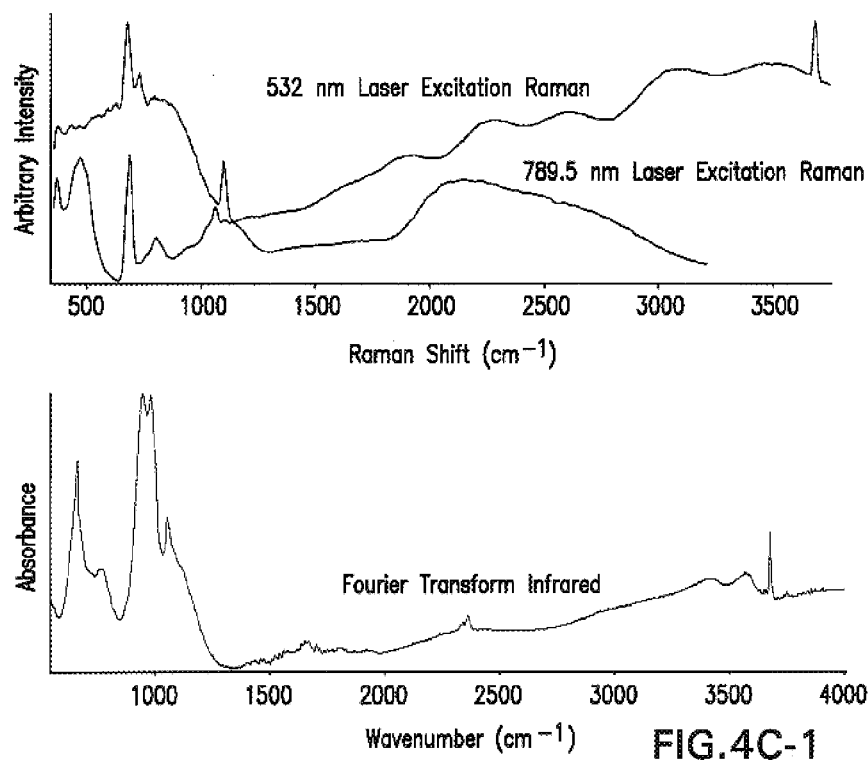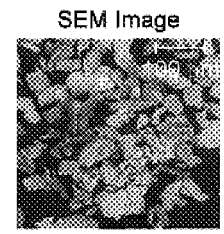
FIG.4C-1  FIG.4C-2

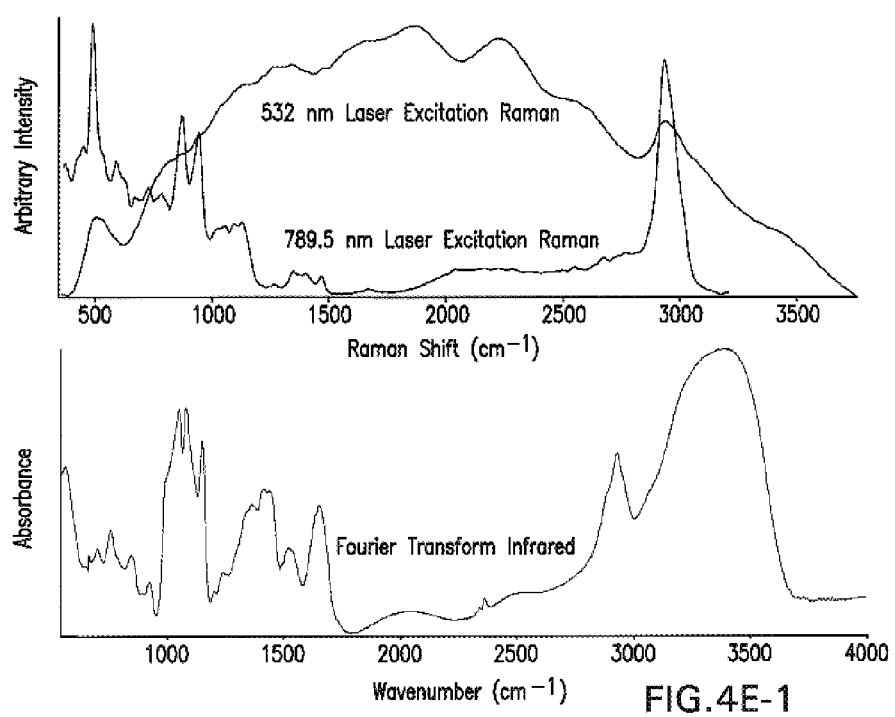
FIG.4E-1  FIG.4E-2

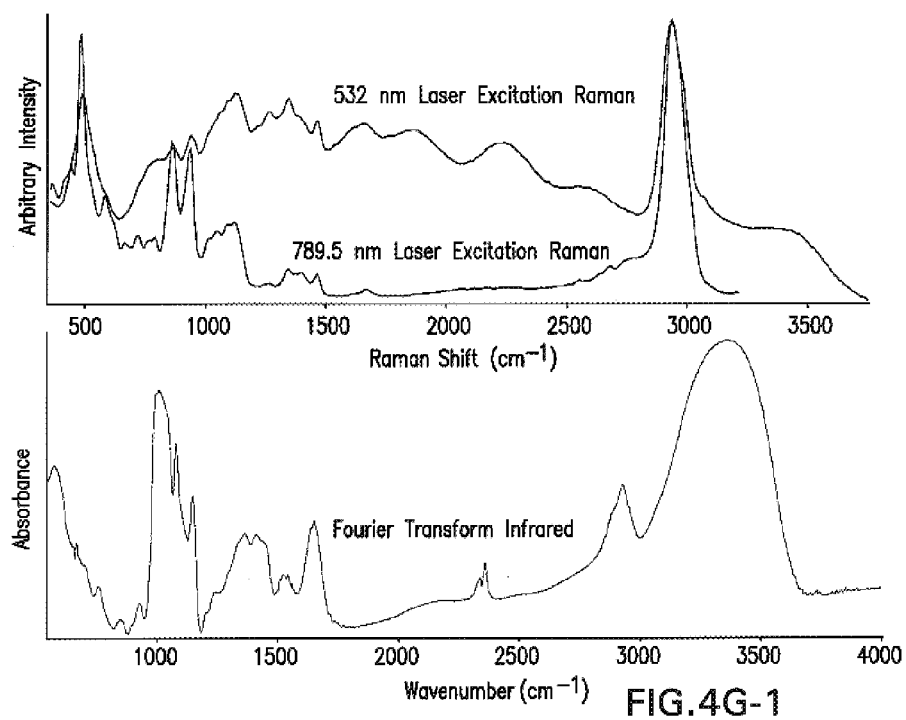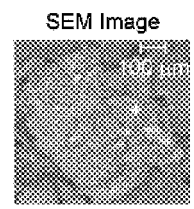
FIG.4G-1   FIG.4G-2

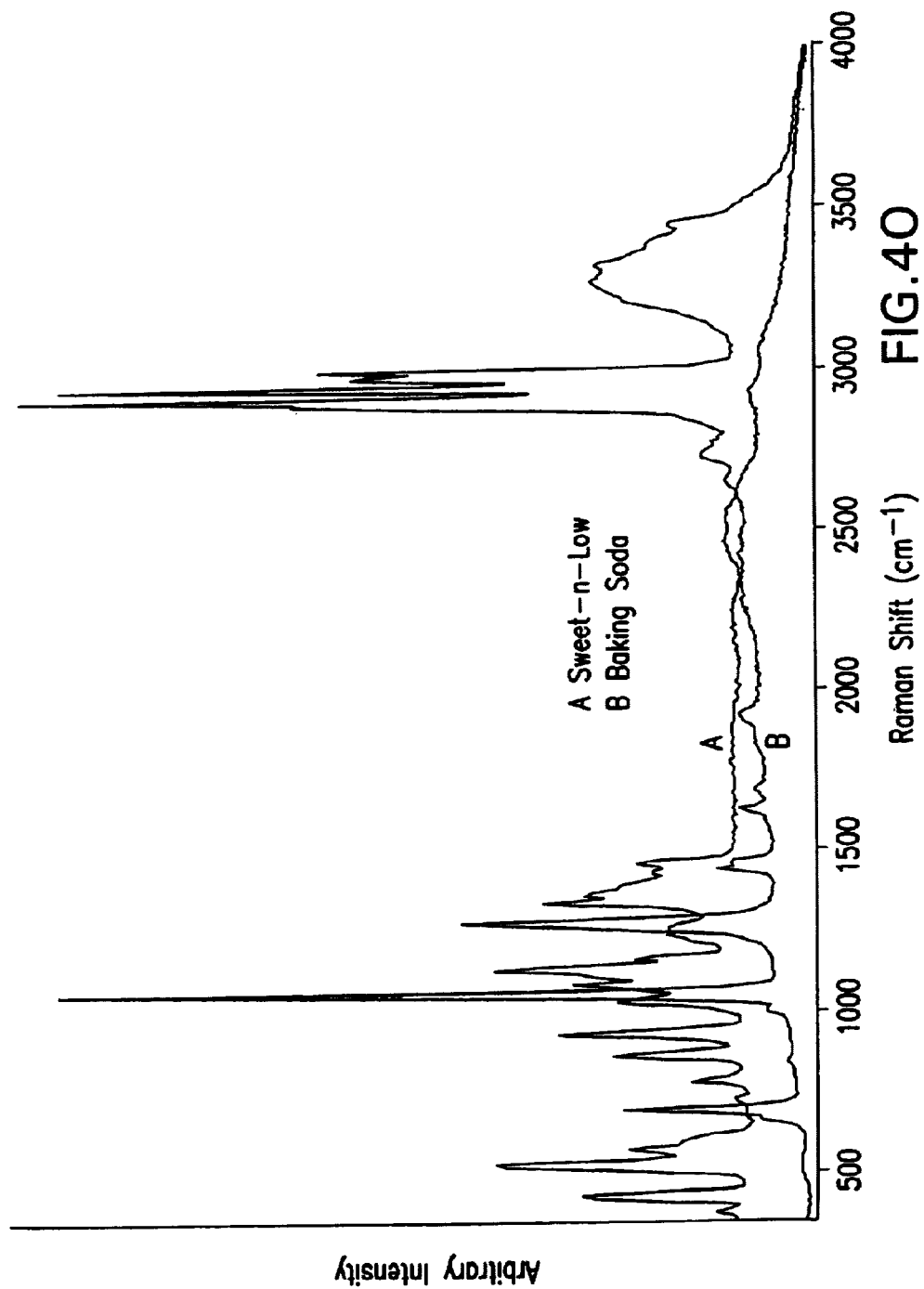

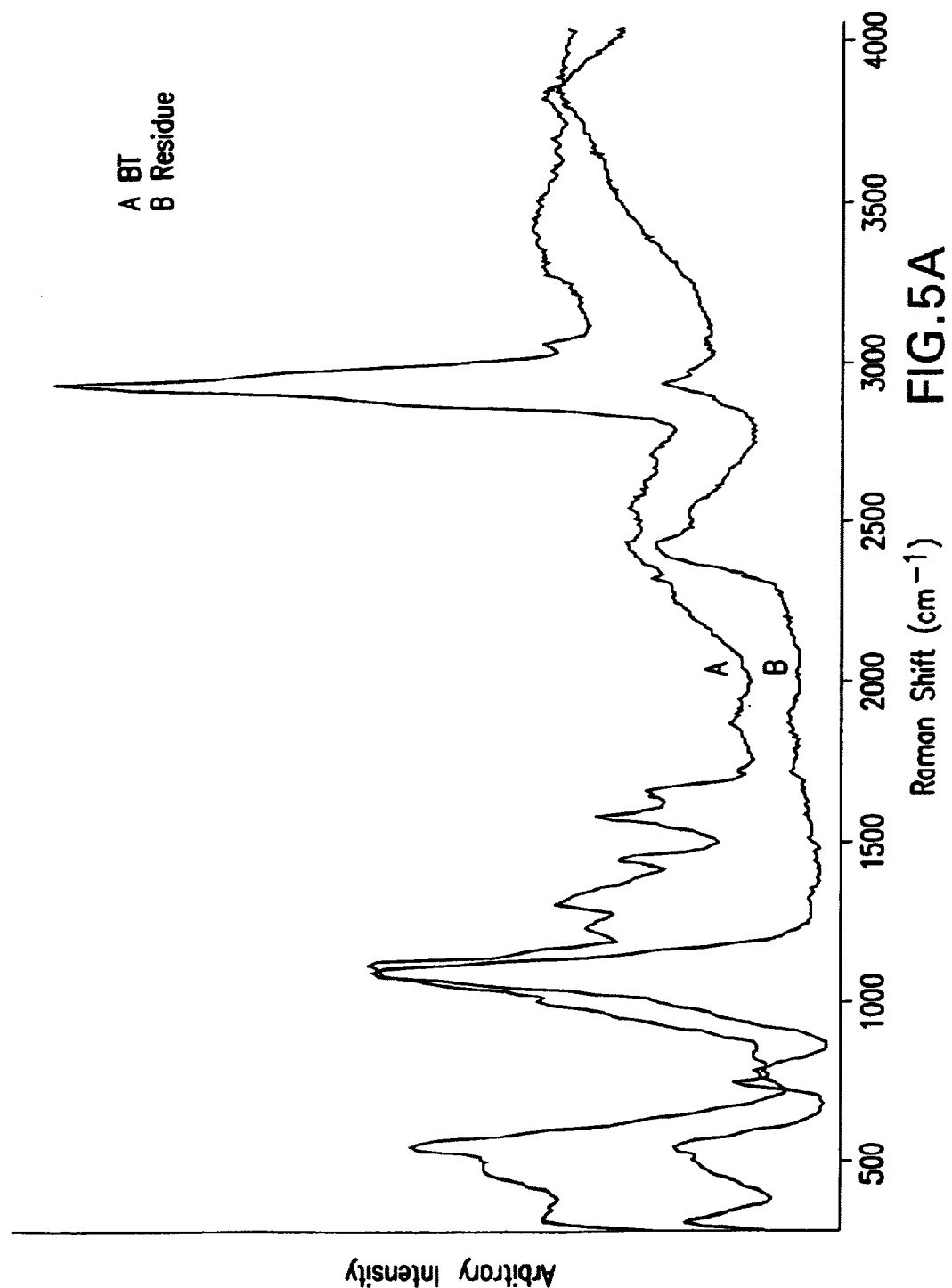

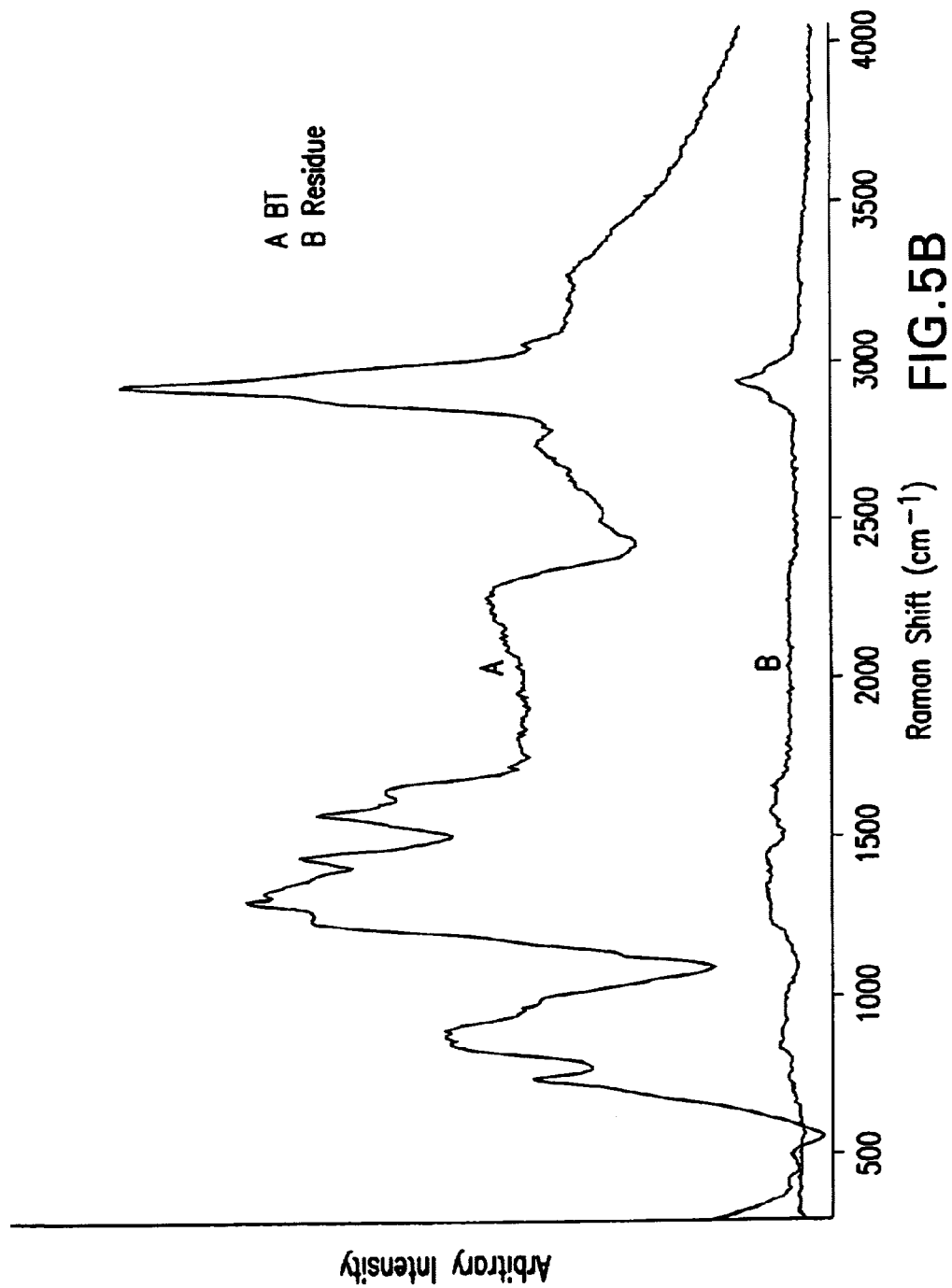

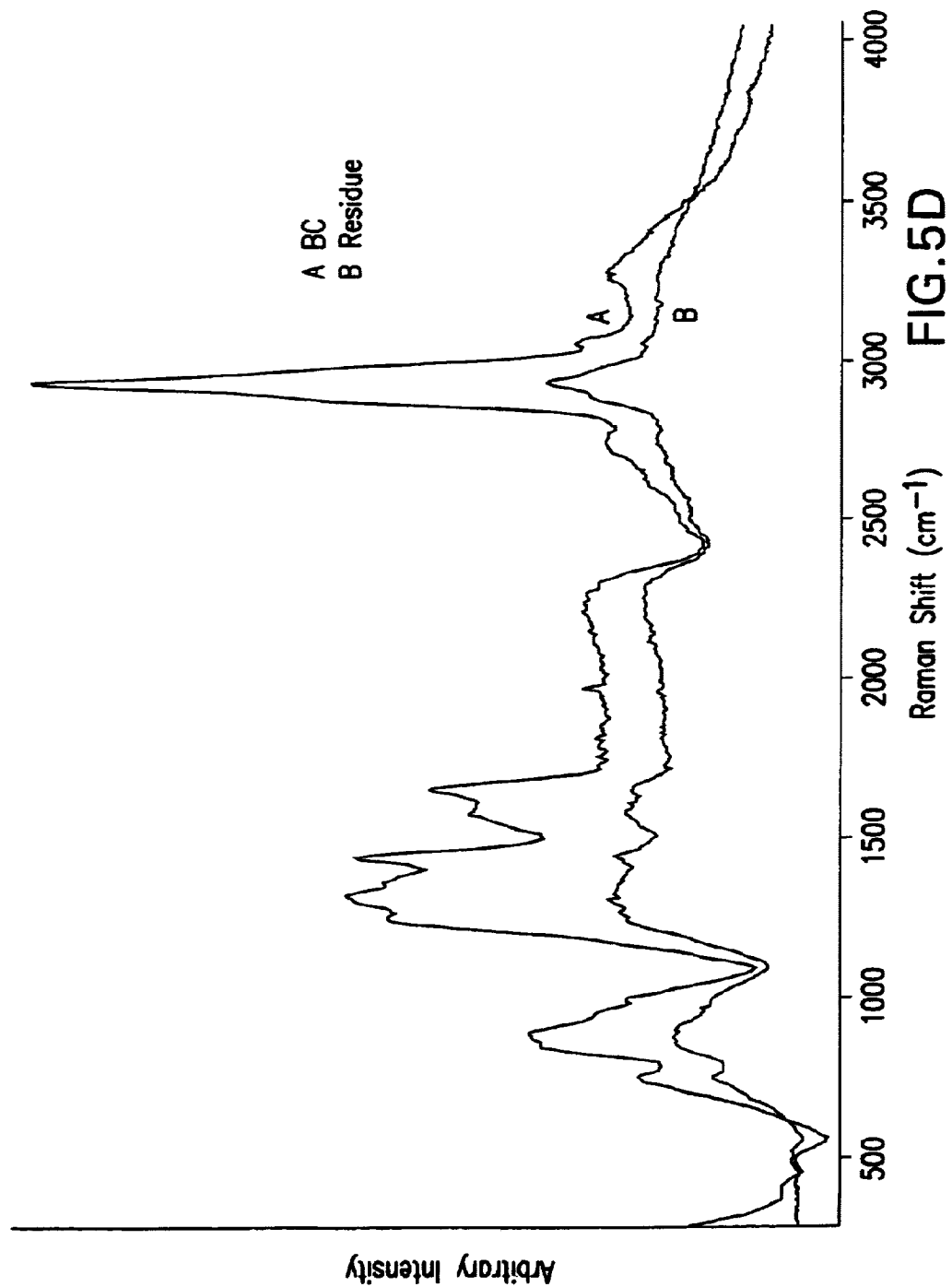

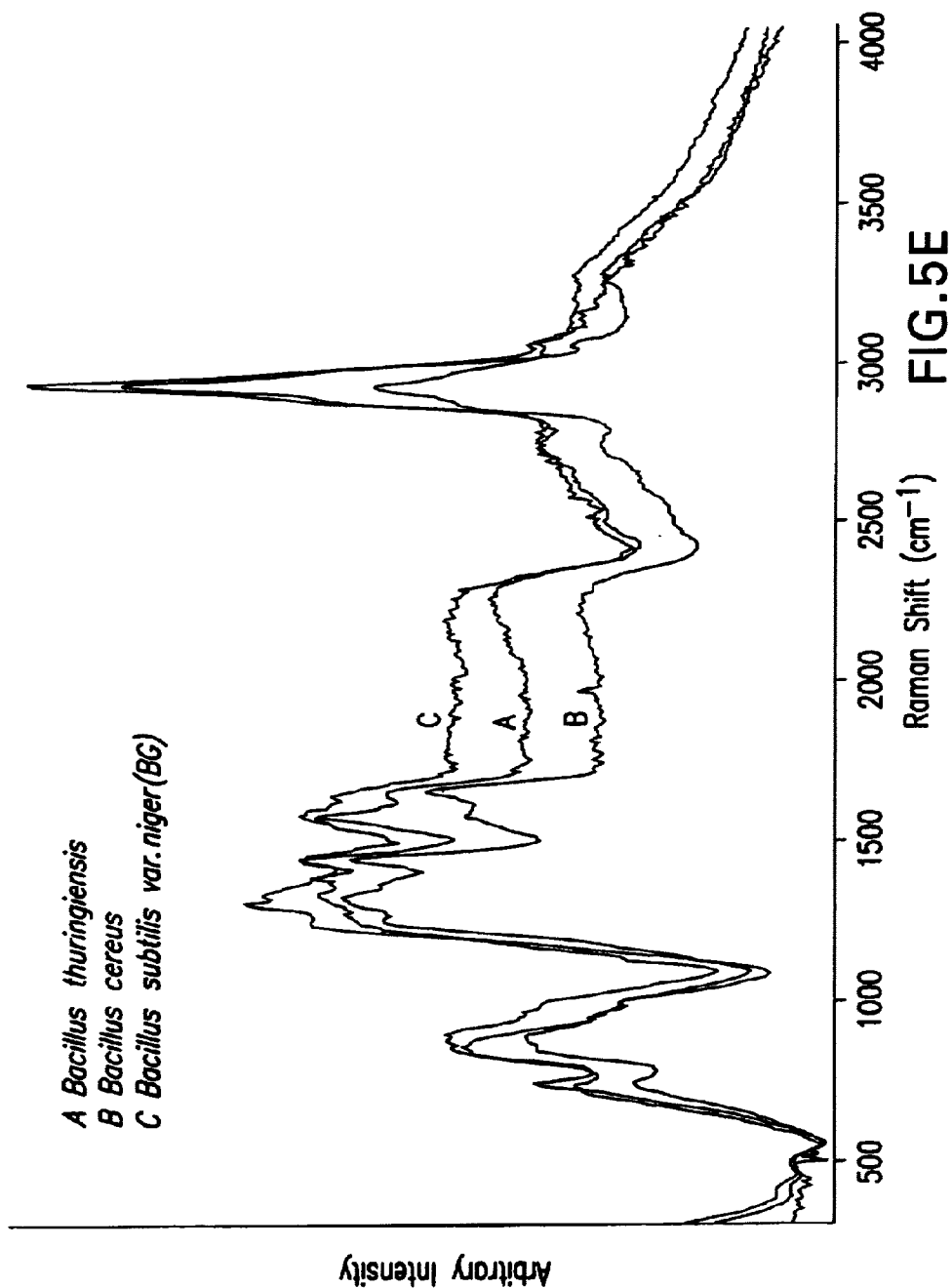

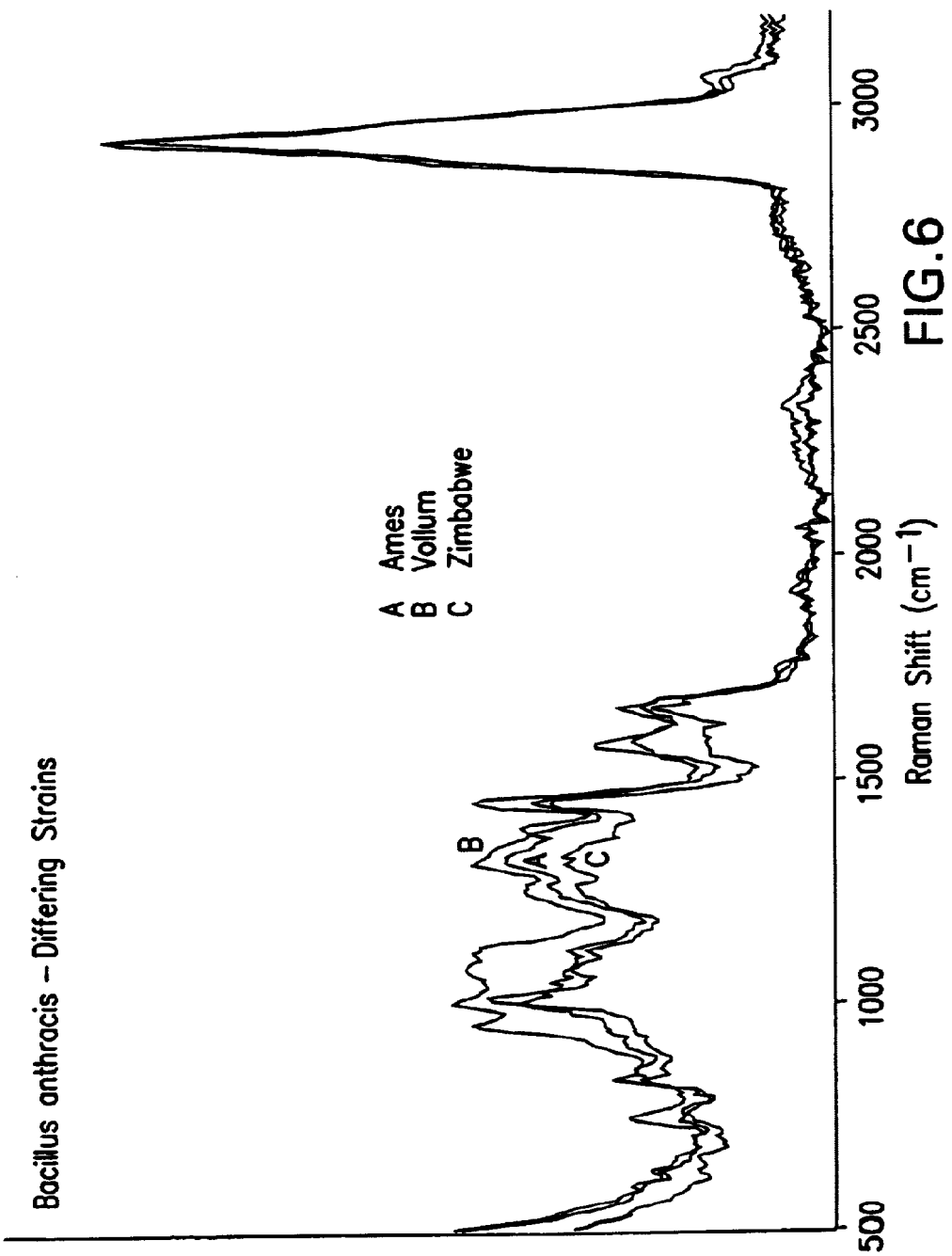

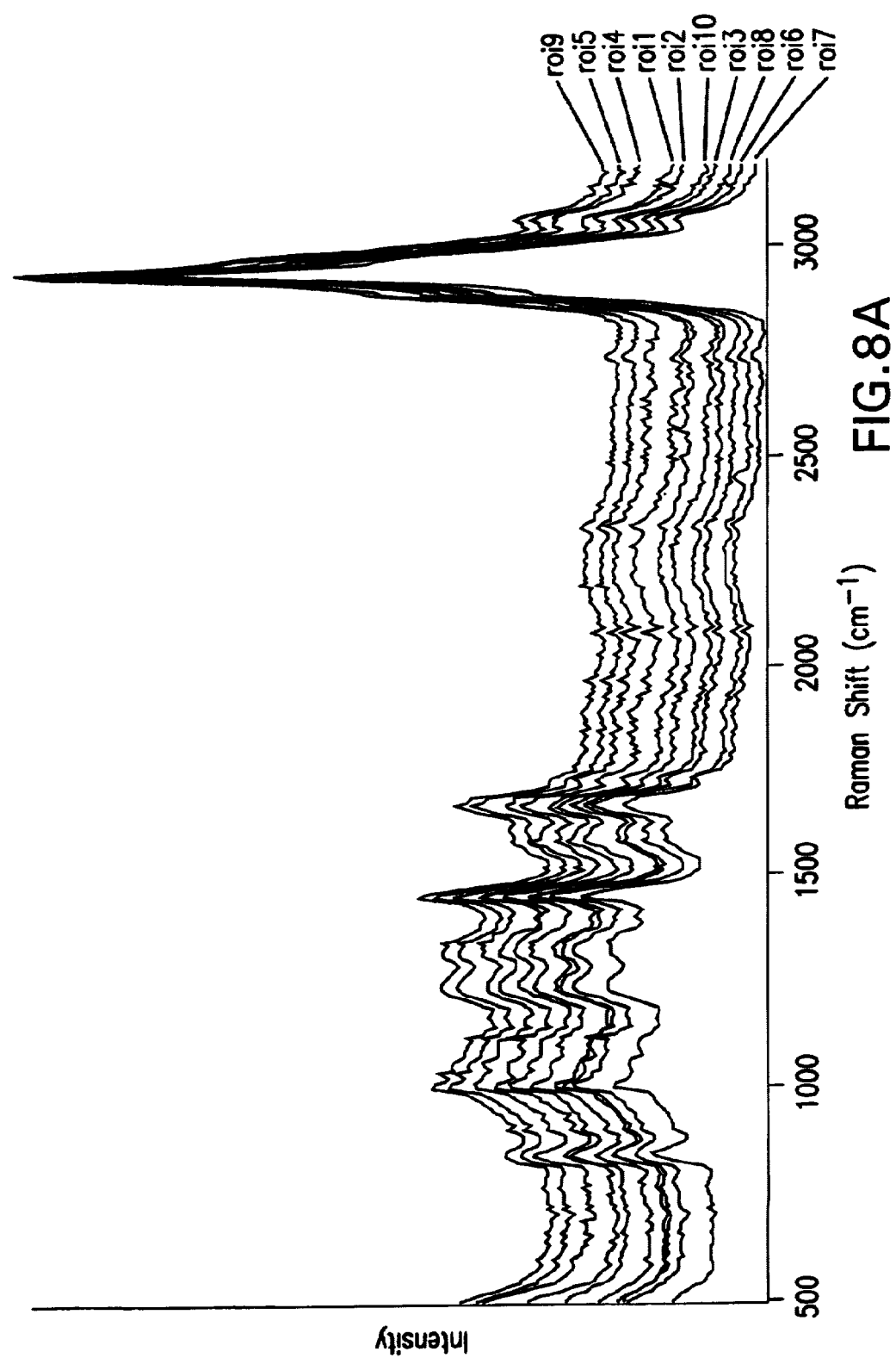

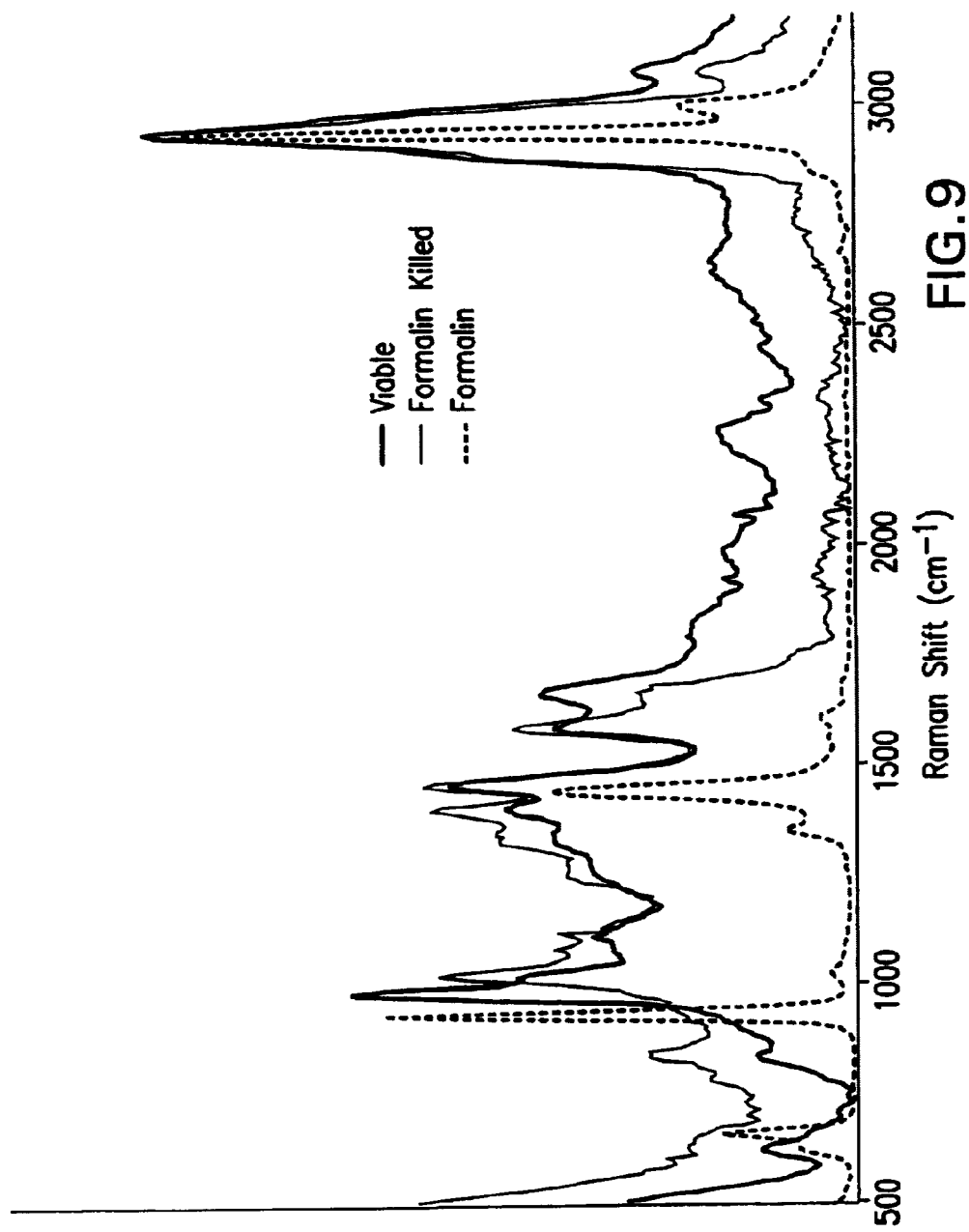

FIG. 11

WIDE FIELD METHOD FOR DETECTING PATHOGENIC MICROORGANISMS

CROSS REFERENCE TO RELATED APPLICATIONS

This application is a continuation-in-part application of U.S. application Ser. No. 10/339,807, filed on Jan. 10, 2003, now issued as U.S. Pat. No. 6,765,668, which itself claims priority from and is related to the now abandoned U.S. Provisional Patent application 60/347,806, filed Jan. 10, 2002.

FIELD OF THE INVENTION

The present invention relates to the field of chemical and biological analysis and more specifically to the use of wide field Raman and fluorescence spectroscopy to quickly identify biological agents and pathogens.

BACKGROUND OF THE INVENTION

Terrorist deployment of chemical and/or infectious biological agents as weapons of mass destruction threatens the welfare of the human populace. Public concern has grown, especially in our nation, as terrorist uses of biothreat agents, such as Anthrax, become reality. Nightmare images of tens of thousands of infected and dying innocent victims strike fear in the hearts of nearly everyone. Biological and chemical warfare is significant, not only in lives lost, but also in the cost to the US economy. The Centers for Disease Control estimates that the loss of 100,000 lives will have a $29 B economic impact. The mass destruction potential of Biological Warfare Agents ("BWAs") and Chemical Warfare Agents (CWAs) is thought by many to be comparable to or even greater than that of nuclear weapons. Nuclear weapons have the potential to affect a finite area, albeit very large, and the use of such weapons is immediately obvious after the fact. BWAs and CWAs, on the other hand, have virtually no boundaries and have the potential to spread silently and unchecked through populations far from ground zero. Likewise, technology to rapidly detect and quantify very low levels of radioactive contamination is widely available. Unfortunately, such technology for BWAs and CWAs at similar levels is not definitive, not widely available and in many cases, is not very rapid.

The psychological impact of this type of threat is also very significant. The public is becoming increasingly aware of new, emerging pathogens. Fear over the unseen nature of BWAs and CWAs make for a very effective terrorism weapon in and of itself. In addition to perception, there is a very real threat due to incredible advances in biotechnology. It is now possible to alter the most virulent bacterium or virus and to increase both its pathogenicity and resistance to conventional therapy. The molecular biology revolution has now been underway for more than three decades, and the sheer number of persons with technical expertise to potentially create such weapons of mass destruction has consequently increased. In this age of advanced global travel, the likelihood of rapid dissemination of any type of BWA worldwide in a very short period of time is high, and the general public is well aware of this fact.

Conventional means of identifying pathogens using biology tools such as specific antibodies, genetic markers or propagation in culture are fundamentally slow and require significant hands-on manipulations. Furthermore, as new BWAs and CWAs are engineered, these conventional tools are likely to become less and less effective. As the use of BWAs and CWAs by terrorists becomes a reality, there is an increasing need to have methods that can rapidly and accurately detect and classify small amounts of these agents at a molecular level without coming into contact with them. Methods are needed that are cost effective and simple to use so that they can be widely deployed. Methods are also needed to help expand our understanding of the biological and chemical basis of such warfare agents and the potential impact on the human body. Furthermore, the knowledge gained through such molecular analyses helps identify new targets for therapeutic and preventative agents.

SUMMARY OF THE INVENTION

A wide field of view observation and spectroscopic detection system, also described as a molecular spectroscopy identification system, employing Raman, fluorescence, UV-visible reflectance/absorption and/or near-infrared (NIR) reflectance/absorption spectroscopic techniques for characterization of BWAs and CWAs is disclosed.

Optical spectroscopy is a widely utilized approach for elemental, molecular or chemical analysis ranging from compounds to organic molecules. Molecular analysis using vibrational spectroscopies allows one to determine the detailed structure and chemical nature of a variety of materials. Such methods are ideal for homogeneous simple materials, such as chemicals, plastics, polymers, etc. Organic biological molecules tend to be far more complicated materials. Microorganisms are significantly more complex and even at the smallest unit, a cell, consist of a complex array of functioning biological structures each made up of their own specific, complex organic biomolecular macro molecules. They include such functional units as a nucleus, microfilaments, plasma membrane, pigments, mitochondria, endoplasmic reticulum, microvilli, lysossomes, centrioles, golgi apparatus and various protective layers. These complex structures and structural/chemical variations gives rise to bio-variability which complicates optical analysis.

Current analytical optical measurements of materials typically fall into either of two categories. One in which a pure batch of the material is available to be measured as a bulk macroscopic sample, i.e. in a large sampling volume, and a second which utilizes micro-analysis techniques to analyze a single small object. In practical situations, sampling of a macroscopic volume does not have the sensitivity to see small concentrations of pathogens, a particularly important need for evaluating BWAs and CWAs. On the other hand, micro-analysis methods allow one to focus on the analysis of an individual microscopic object by using a highly focused excitation beam. Such focused beam optical methods are effective for inorganic and organic particulates but can be ineffective for microorganisms due to their bio-variability and sensitivity to irradiation. Bio-variability comes in two forms: one from variations in the signal from different locations in the microorganism, i.e. the sampling probe is smaller than the organism, and the other from small variations between the same type of organism. In addition, biological microorganisms can decompose or 'burn' under the high power density of the highly focused incident beam. This requires reducing the optical radiation on the microorganism so as to not destroy any one organism and thereby collecting optical emission for longer times to compensate for the reduced irradiation intensity. To reduce the effects of bio-variability, sampling many small objects is also needed. Thus use of optical microanalysis methods to sequentially sample many organisms thereby becomes very time consuming. Our approach removes these limitations by using a wide field of view and a wide field of optical excitation to average the optical emission from a small plurality of pathogenic microorganisms. The resulting sensitivity allows us to detect and reliably identify a few microorganisms even in the presence of a matrix of foreign material, i.e. so called 'masking agents'.

Infrared, Raman, visible reflectance, fluorescence and near Infrared optical spectroscopies has been applied to detect microorganisms with limited success. Infrared and Raman spectroscopies can provide spectrally rich fingerprint information, while fluorescence can be used if specific fluorescent features arise. Complicating the application of optical scattering techniques is the fact that many materials exhibit a broad fluorescent background under visible illumination. Such fluorescence creates a significant spectral background that can obscure the spectral pattern of other objects in the filed of view being analyzed. This background typically varies along the substrate particularly when dealing with real samples that contain a variety or mixture of components. We find that these spatially dependent fluorescent backgrounds can be significantly reduced by irradiating an area slightly larger than the sampling area with the optical probe beam. This reduction is referred to as photobleaching. This together with using a wide field of view to encompassing a small plurality of microorganisms enables this invention to routinely and accurately be applied to detect these microorganisms.

This removal of interfering fluorescence signals differs from other methods where adding fluorescence helps. Fluorescent ligands can be introduced that are engineered to bind to certain biomolecular features in these organisms. These usually involve some bio-active agent, such as antibodies, that recognize and attach to specific biomolecular features. Here the fluorescent ligands then act as a marker, label or tag for these organisms or parts of these organisms. While such external fluorescent markers/tags can add contrast to aid in the optical detection of specific biological features, organisms or bio-materials, they represent a consumable, problematical reagent that adds cost, time and additional handling to the detection process.

Optical methods such as Raman and Infrared also have significantly weaker signals from biological macromolecules than from pure chemicals and so benefit from some sort of signal amplification to detect small concentrations. In Infrared this can include multiple reflections off the sample to augment the resulting signal. However, this then requires some specialized sample size or sampling configurations which will limit the application or increase the cost of the sampling device. In Raman spectroscopy the signal can be enhanced by using special substrates that enhance the Raman signals by 3 to 7 orders of magnitude. However, not all molecules bond to SERS active surfaces which limits the application of such an approach. Our invention does not require special substrates and improves the signal to noise by using a wide field of view.

To enhance Raman signals, Resonance Raman has also been employed for biological systems by using higher energy optical radiation (wavelengths smaller than about 400 nm) to excite the biomolecule or biological organism. While Raman signals are enhanced at the resonance conditions, the higher excitation energy excites electronic states of the biomolecules thereby producing larger laser power absorption and heating by the sample which can degrade or damage the microorganism. In addition, the optical components and UV detectors needed to support UV illumination and sensing are also more expensive and specialized than commonly used visible light optics components.

This invention teaches how to utilize wide field optical spectroscopy for the detection of pathogenic microorganisms that circumvents many of the shortcomings and limitations of many possible optical spectroscopies that can be applied to detect small concentrations of microorganisms. Our wide field molecular spectroscopic method reduces several artifacts and inherent sampling problems so as to permit highly reliable determinations which are not anticipated by prior work nor has it been realized to date, despite the wide body of Raman spectroscopy practiced today. Our method utilizes an optical spectroscopic system, our wide field illumination approach and a digital spectral pattern recognition system to recognize pathogenic microorganisms. Unlike prior methods, this method provides high sensitivity and makes identification of pathogenic microorganisms both reliable and practical.

A key element of this invention is the use of a wide field of view for viewing and irradiating controlled regions of the target substrate together with the collection and analysis of the optical emission from the same area of the wide field of view. We define wide field of view as an area which is equal to or larger than the microorganism under study. Our invention uses several methods to address several critical problems arising with conventional optical methods used to identify microorganisms.

The most widely applied Raman method for the study of microscopic biological systems utilizes micro-Raman spectroscopy. Here a tightly focused beam of an already collimated laser results in an illumination spot size of about 1 micron and smaller to maximize the Raman signal intensity on the target of interest. Such highly focused beams can destroy the microorganism while attempting to measure it. Reducing the power in the irradiating beam will require long data acquisition times. Further the use of such small spot sizes can lead to nonreproducible signals given the biovariability of the microorganisms as they are distributed at various locations in the specimen being analyzed. In addition the fluorescence background signals typically vary with time and at different regions of the sample, further interfering with detecting pathogenic microorganisms.

This invention considers an overlooked alternative methodology to target, irradiate and detect microorganisms and thereby represents a novel approach for microorganism detection. Targeting is comprised of finding a region of the substrate which has several suspect features which are characteristic of pathogen masking materials or various features of the pathogen itself, such as shape, size or color of spores, powder, agglomerates or clumps as well as fluorescence features within these objects. This can be done via manual inspection or using automated image recognition techniques from an optical viewing device. Once targeting is complete, the magnification is increased and a smaller area is selected to allow the collection of a larger solid angle of optical emission produced from Raman or fluorescence excitations within the targeted area. This region when viewed by the optical viewing means still reveals a wide field of view of the target material rather than a single microscopic object. The excitation source for spectroscopy then illuminates a region around this wide field of view at sufficiently high power densities to photobleach this region and allow stable optical spectra to be obtained. The slight overfilling is advantageous in that it eliminates spectral changes associated with slight shifts or changes in the sample position during the acquisition of the spectra as well as subsequent nearby data acquisition in neighboring areas within the irradiated area. Illuminating approaches using broad flood illumination over regions substantially larger than the wide field of view do not provide sufficient power for adequate photobleaching. The acquisition of the Raman scattered light is done over the wide field of view to efficiently collect and average spectra from a small plurality of microorganisms which is then analyzed for the spectral features of pathogenic microorganisms. This wide field sampling approach provides several critical advantages over spot or line focused excitation sources used for Raman spectroscopy. Unlike many optical micro analysis methods, we utilize a non-confocal infinity corrected optical system and view the target area in a wide filed of view with an objective that provides a high numerical aperture. In contrast to other methods that concentrate the power onto the object of study, we defocus the optical beam over the field of view used. Overall this method allows the following improvements over currently used spectroscopy methods:

1. Efficient photobleaching of substantial areas of the sample under investigation reduces the overall fluorescent background signal to enhances signal to noise and avoids local fluorescent variations that degrade signal to noise that typically arise with conventional micro analysis instruments.
2. The wide field of illumination reduces biological signal variability, improves thermal management, increases signal levels and reproducibility.
3. The wide field of emission improves signal to noise of the target pathogenic microorganism.
4. The ability to visualize and select areas of the substrate either manually or automatically based on some objective measures of the specimen or target microorganisms such as, for example, the intrinsic size of the organism, enhances signal to noise.
5. The use of a similar wide field for viewing, irradiation and emission assures that a well defined and appropriate area on the substrate is selected for analysis.
6. The configuration and approach used allows low cost compact spectrometers, for example those having simple wavelength dispersive elements, with sufficient resolution to detect the spectral components emitted from the specimen being investigated. The effective use of such scalable optical elements with this wide field method will enable such inspection systems to be scaled down to smaller sizes thereby enabling a portable handheld unit.
7. A variety of substrates can be used for the microorganisms for this analysis thereby allowing greater flexibility for this method. Many materials on which the material may arise can also be used as substrates, such as for example, paper.

Wide area irradiation and detection requires some simple sample preparation Sample preparation involves collecting and placing the sample in a thin, uniform layer. Selecting a target area for such preparations requires establishing a correct image profile such as size and shape. The target density will determine the field of view used and the irradiation intensity that is required which are both based on calibration data obtained or calculated beforehand. Such calibration curve are readily created by one skilled in the art.

In one embodiment, Raman micro-spectroscopy and/or fluorescence micro-spectroscopy can be used to detect, classify, and/or identify BWAs, CWAs and non-threatening compounds. Micro-dispersive spectroscopy detects, classifies and identifies materials including single bacterium. An appropriate digital analysis of the resulting Raman spectra can resolve the target microorganism signal from BWAs and CWAs in the presence of non-threatening 'masking' compounds.

In another embodiment, fluorescence and Raman macro-spectroscopy can be used to detect, classify, and/or identify BWAs, CWAs and non-threatening compounds. These macro-spectroscopy techniques can perform sub-millimeter size particle detection, classification, identification of BWAs and CWAs (i.e., agglomerated bacteria and endospore detection and identification). In addition, fluorescence and Raman macro spectroscopy can perform detection, classification, and identification of BWAs and CWAs in the presence of non-threatening 'masking' compounds when appropriate data analysis techniques are applied.

In an another embodiment, Raman fiber optic based spectroscopy can detect, classify and/or identify BWAs, CWAs and non-threatening compounds when appropriate data analysis techniques are applied.

These different embodiments all can utilize a computer analysis method to compare the observed optical spectra to known optical spectra obtained under similar conditions to identify the microorganism.

The system and methodology described above are applied in a variety of modes. The system is applied as a laboratory or transportable field Raman microscope which integrates a dispersive Raman spectrometer and digital data analysis module. The system is also applied as a UV/Vis/NIR fluorescence, Raman, or UV/Vis/NIR/Mid-IR absorption/reflectance macroscope system such as ChemImage's CONDOR Macroscope. Alternatively, the system is applied as a laboratory or field fiberscope such as ChemImage's RAVEN endoscope. Each of the modes of application are used separately or in combination with one another to achieve the desired speed and results. In addition, the properties of the wide area detection method are scalable down to the size of the wide area being investigated thereby allowing the miniaturization of the required hardware to enable a hand held device with local sampling and/or remote analysis capabilities.

Spectroscopic techniques are applied to sensors designed to detect, classify, identify BWAs, CWAs and non-threatening compounds in ambient air. A schematic of such a sensor is shown in FIG. 1. The vacuum created by an air-sampling pump pulls the ambient air through the sample inlet and through the filter. Filter materials could include porous polypropylene or cellulose, in disk or roll form. Particulates in the air sample are trapped on the surface of the filter medium and are held in the field of view of the spectroscopic imaging system. The source, chosen specifically for the type of molecular spectroscopy being used, illuminates a wide area of the trapped particles and induces either Raman or fluorescence emission from the sample. The emitted emission is collected and refocused into a detector that measures the emitted light at a series of wavelengths and creates the data file used for further analysis. The inlet to this detector can either be an imaging optical fiber or conventional optics. Advanced chemometric techniques along with a database of known spectra are used to detect, classify, and/or identify BWAs, CWAs and non-threatening compounds.

The system can be automated through the use of robotics or combined macro/micro instrumentation in order to target BWAs, CWAs and non-threatening agents. Using laser ablation and/or chemical ablation, the system can be automated to eradicate BWAs and CWAs post-targeting.

A variety of data processing procedures can be used with the system. A weighted spectral data subtraction routine can be used to suppress contribution from the substrate or microscope slide. Alternatively, multivariate image analysis involving principal factor analysis and subsequent factor rotation can be used for differentiation of pure molecular features in BWAs, CWAs and non-threatening 'masking' compounds.

BRIEF DESCRIPTION OF THE DRAWINGS

FIGS. 4A through 4Q show the preliminary results of dispersive spectroscopic examination of samples sent by the US Armed Forces Institute of Pathology (AFIP), experts in the objective assessment of biothreat detection technologies. These samples include 6 unknown powders and a sample of BG spores.

FIG. 4A shows dispersive Raman spectra (green laser excitation) of the 6 unidentified powders through the vials.

FIG. 4B shows dispersive Raman spectra (red laser excitation) of the 6 unidentified powders.

FIGS. 4C–4E (Sample 1331-002) show dispersive Raman, IR and SEM-EDS results on a first of the 6 unidentified powders. The sample is inorganic and most likely talc.

FIGS. 4E–4F (Sample 1325-002) show dispersive Raman, IR and SEM-EDS results on a second of the 6 unidentified samples. The sample is organic and most likely starch, possibly corn starch.

FIGS. 4G–4H (Sample 1303-002) show dispersive Raman, IR and SEM-EDS results on a third of the 6 unidentified powders. The sample is organic and most likely starch, possibly corn starch.

FIG. 4O shows the Raman spectra of common white powders used as masking agents.

FIG. 4Q shows a wide field Raman Image where the 2 similar spores are differentiated on the basis of autofluorescence differences.

FIGS. 5A through 5F show the results from additional spore samples selected specifically because the inherent difficulty in differentiating these species. They include *Bacillus thuriengensis* (BT), *Bacillus cereus* (BC) and BG. The Raman spectra from the 3 spores are different. These differences suggest a good chance of differentiating anthrax from non-threats. The details follow:

FIG. 5A shows raw dispersive Raman spectra of BT and the suspension residue. The residue is from the suspension liquid.

FIG. 5B shows background corrected spectra of BT and residue. Both the spores spectrum and residue spectrum have been divided by a spectrum of the microscope slide.

FIG. 5C shows raw dispersive Raman spectra of BC and the suspension residue.

FIG. 5D shows background corrected dispersive spectra of BC and residue

FIG. 5E shows a compilation of sample BT, BC and BG dispersive spectra with microscope slide background correction. The spectra are different. The differences are greatest in the fingerprint region.

FIG. 5F shows a compilation of the 3 spores after baseline subtraction and normalization to the CH region spectral feature (~2950 $cm^{-1}$).

FIG. 6 shows how Raman spectra can be applied to distinguish between multiple bacterial strains within a single species.

FIG. 9 shows how dispersive Raman spectra can be applied to distinguish between viable and non-viable endospores, a critical variable in determining real threat level.

FIG. 11 shows ROC curves obtained from a dispersive spectrometer using this wide field method and our digital spectral analysis that demonstrates high sensitivity and selectively in detecting Anthrax.

DETAILED DESCRIPTION OF THE PREFERRED EMBODIMENTS

Figure 2B:
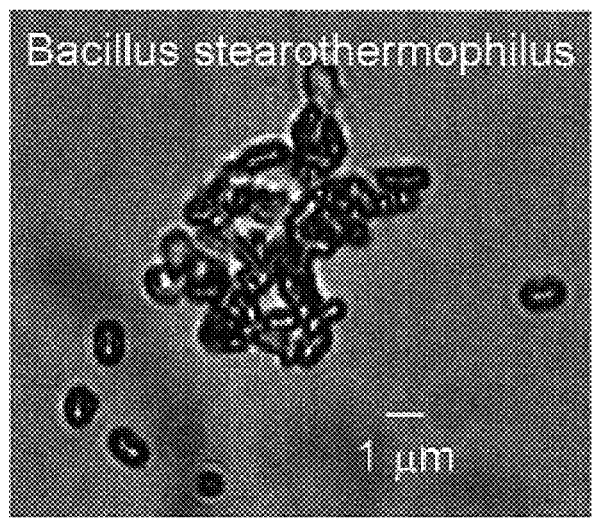
FIG. 2 shows a wide field dispersive Raman spectra of three different bacterial spore types including an Anthrax simulant.

Methods of Raman chemical imaging and spectroscopy are extensively covered in the following United States patents and patent applications assigned to the assignee of the present invention: U.S. Pat. No. 6,002,476; U.S. Non-Provisional Application Ser. No. 09/619,371 filed Jul. 19, 2000; U.S. Non-Provisional Application Ser. No. 09/800,953 filed Mar. 7, 2001; U.S. Non-Provisional Application Ser. No. 09/976,391 filed Oct. 12, 2001; U.S. Non-Provisional Application Ser. No. 10/185,090 filed Jun. 28, 2002; U.S. Non-Provisional Application Ser. No. 10/184,580 filed Jun. 28, 2002; U.S. Provisional Application 60/144,518 filed Jul. 19, 1999; U.S. Provisional Application No. 60/347,806 filed Jan. 10, 2002; U.S. Provisional Application No. 60/187,560 filed Mar. 7, 2000; U.S. Provisional Application No. 60/239,969 filed Oct. 13, 2000; U.S. Provisional Application No. 60/301,708 filed Jun. 28, 2001; U.S. Provisional Application No. 60/422,604 filed Oct. 31, 2002.

The above identified patents and patent applications are hereby incorporated by reference, including referenced material.

Spectroscopy is the study of the interaction of light and matter. Light can be absorbed, reflected, transmitted, emitted or scattered by a substance at characteristic wavelengths (i.e., colors) of the electromagnetic spectrum (incl. gamma ray, X ray, ultraviolet (UV), visible light, infrared, microwave, and radio-frequency radiation) upon excitation by an external energy source. These characteristic wavelengths can then lead to the identification of the material's elemental and/or molecular composition. Experiments typically consist of a light source, a light-dispersing element (i.e., prism or grating) to create a spectrum and a detection device.

In Raman spectroscopy, the photons of interest are scattered by the material. If the incident light is monochromatic (single wavelength) as it is when using a laser source, a small fraction of the scattered radiation differs in frequency (wavelength) from that of the laser. Furthermore, frequencies of the scattered light are unique to the molecular species present. This phenomenon is known as the Raman effect.

In Raman spectroscopy, energy levels of molecules are probed by monitoring the frequency shifts present in scattered light. A typical experiment consists of a monochromatic source (usually a laser) that is directed at a sample. Several phenomena then occur including Raman scattering that is monitored using instrumentation such as a spectrometer and a charge-coupled device (CCD) detector.

Similar to an infrared spectrum, a Raman spectrum reveals the molecular composition of materials, including the specific functional groups present in organic and inorganic molecules. Raman is useful because the spectral response exhibits a characteristic 'fingerprint' spectrum, subject to various selection rules. Peak shape, peak position and the adherence to selection rules can also be used to determine molecular conformation information (crystalline phase, degree of order, strain, grain size, etc.). Unlike infrared spectroscopy, a single Raman spectrometer can be applied to the molecular characterization of organic and inorganic materials simultaneously. Other advantages of Raman over traditional infrared spectroscopy include the ability to analyze aqueous phase materials and the ability to analyze materials with little or no sample preparation. Deterrents to using Raman spectroscopy as opposed to infrared spectroscopy include the relatively weak nature of the Raman phenomenon and interferences due to fluorescence. In the past several years, a number of key technologies have been introduced into wide use that have enabled scientists to largely overcome the problems inherent to Raman spectroscopy. These technologies include high efficiency solid-state lasers, efficient laser rejection filters, and silicon CCD detectors.

In fluorescence spectroscopy, photons are emitted from a material following an excitation step in which absorption of photons occurs. Experiments typically include a polychromatic excitation source such as mercury (Hg) or xenon (Xe) lamps or a monochromatic source such as a laser for sample excitation. A portion of the emitted radiation may then be directed into a dispersive monochromator to which a detector device such as a CCD is attached. By measuring the fluorescence spectrum from a material, one can deduce qualitative and quantitative information from inorganic and organic species. In comparison to Raman spectroscopy, fluorescence is inherently more sensitive. Detection limits in the parts-per-billion are common. On the other hand, fluorescence is less selective than Raman and not all chemical systems that exhibit fluorescence.

Molecular UV/visible and NIR absorption spectroscopies involve the absorption of photons throughout the UV/visible (185–780 nm (54,054 to 12,800 $cm^{-1}$)) and NIR (780 nm–2.5 μm (12,800 to 4,000 $cm^{-1}$)) spectral regions, respectively. Typical instrumentation include a polychromatic source such as a deuterium or quartz tungsten halogen lamp, a dispersive element such as a monochromator or interferometer and a detection device such as a Si CCD or InGaAs focal plane array detector. Absorption measurements based upon UV-visible or NIR radiation find a wide number of applications for both qualitative and quantitative determination of inorganic and organic species. NIR spectra result from the overtone and combination bands of fundamental mid-infrared (MIR) bands. Like fluorescence, absorption spectroscopies are highly sensitive but only moderately selective.

Raman spectroscopy is a versatile technique that is well suited to the analysis of simple and complex heterogeneous materials. Applications of spectroscopic analysis range from the analysis of polymer blends, defect status analysis in semiconductor materials, inclusions in human breast tissue, characterization of corrosion samples and detection, classification and now to the identification of BWAs and CWAs. Wide filed Raman spectroscopy combined with digital spectral analysis provides a potential solution for obtaining both qualitative and quantitative information about molecular composition rapidly at reduced cost and higher speed than other spectroscopic methods as well as imaging or 'wet' chemical methods.

Wide Field Raman Spectroscopy and digital spectral processing respectively combines Raman, fluorescence, UV/visible absorption/reflectance and NIR absorption/reflectance spectroscopies with digital processing for the molecular-specific analysis of materials. This enabling technology allows spectra of samples to be recorded at discrete wavelengths (energies). A spectrum is generated from all points of the sample surface by tuning the Raman spectrometer over a range of wavelengths and collecting the signal intermittently. Depending on the materials and the spectroscopic method of choice, depth-related information can also be obtained by using different excitation wavelengths or by capturing spectroscopal information at incremental planes of focus. Contrast is generated in the material under study based on the relative amounts of Raman scatter, fluorescence emission, UV/visible absorption/reflectance or NIR absorption/reflectance that is generated by the different species located throughout the sample. Since a spectrum is generated from several of the component materials at one time, digital analysis methods such as chemometric analysis using correlation analysis, Principal Component Analysis (PCA) and factor rotation, including Multivariate Curve Resolution (MCR) are applied to spectral data to extract pertinent information otherwise missed by ordinary univariate measures.

Instantaneous Anthrax Detection System Based upon a Wide Field Raman Spectroscopic Instrumentation There are a number of immediate instrumentation configurations based on wide Field Raman spectroscopy that may meet the key instrument requirements outlined previously necessary to be an effective, instantaneous Anthrax detection system. These configurations include platforms based on a microscope, a macroscope, an endoscope, an air sampler design or a handheld design. Each of these is outlined briefly below.

Microscope-Based System

The wide field micro-spectroscopic system combines in a single platform a solid state laser for sample excitation (Raman and laser-induced fluorescence only), a refractive optical microscope base, which is equipped with infinity-corrected microscope objectives, an automated XYZ translational microscope stage and a quartz tungsten halogen (QTH) lamp and/or a mercury (Hg) lamp. Also a part of the microscope system is an analog color charge-coupled device (CCD) detector for ordinary optical image collection and a spectrometer dielectric or other bandpass filter, and a optical monochromator equipped with a CCD detector for spectral collection. Such optical monochromators come in many varieties involving tunable filters, line or spot focused dispersive elements or Fourier transform spectrometers. Also included is either a room temperature or optionally cooled IR FPA for IR image capture or a thermoelectrically cooled (TE) Si CCD detector for UV/visible, and fluorescence spectral capture. A remote, UV, visible or NIR illumination is directed to the sample in a reflected light configuration using a QTH source or other broadband white light source, including metal halide, Hg arc lamps or Xe arc lamps or a transmitted light configuration using QTH or other suitable source of a refractive optical microscope platform. In a Raman or laser-induced fluorescence experiment, laser radiation is introduced to the sample through use of a Raman illuminator. Light scattered, emitted, reflected or transmitted is collected from the sample positioned on the automated XYZ translational microscope stage through an infinity-corrected microscope objective. In each illumination scheme, a wide field of illumination is chosen to optimize the quality and reliability and integrity of the sample under investigation.

Ordinary optical imagery of the emission can be obtained using a mirror or beamsplitter or prism arrangement inserted into turret wheel of the microscope and collecting an image with an analog or digital color or monochrome charge-coupled device (CCD) or CMOS detector. An entire spectra can be obtained over the wide field/area collected or a magnified spectroscopic image is coupled through an imaging spectrometer and collected on a NIR or mid-IR focal plane array (FPA) detector (for IR spectroscopic imaging) or a Si CCD detector (for UV/visible absorption/reflectance, fluorescence and Raman spectroscopic imaging. The IR FPA is typically comprised of indium gallium arsenide (InGaAs), but may be comprised of other IR sensitive materials, including platinum silicide (PtSi), indium antimonide (InSb) or mercury cadmium telluride (HgCdTe).

A central processing unit, typically a Pentium computer, is used for spectroscopic intensity versus wavelength collection and processing. The analog color CCD, IR FPA and/or Si CCD, automated XYZ translational microscope stage controlled via a controller and liquid crystal or other imaging spectrometer (through the appropriate imaging spectrometer controller) are operated with commercial software, such as ChemAcquire (ChemImage Corporation) in conjunction with ChemAnalyze (ChemImage Corporation.).

Spectrometers of the following types can also be utilized: fixed filter spectrometers; grating based spectrometers; Fourier Transform spectrometers; or Acousto-Optic spectrometers. A polarization independent interferometer such as a: Michelson interferometer; Sagnac interferometer; Twynam-Green Interferometer; Mach-Zehnder Interferometer, may be used as a filter. Spectrometers designs that allow optical scaling to small sizes are preferred to enable more portable field deployable devices.

The wide field spectroscopic method can be used for depth measurements through the means of moving the sample through focus in the Z, axial dimension, collecting data in and out of the focal plane and reconstructing a volumetric profile of the sample in software. For samples having some volume (bulk materials, surfaces, interfaces, interphases), volumetric spectroscopic imaging has been shown to be useful for failure analysis, product development and routine quality monitoring. The potential also exists for performing quantitative analysis simultaneous with depth analysis. Volumetric imaging can be performed in a non-contact mode without modifying the sample through the use of numerical confocal techniques, which require that the sample be measured at discrete focal planes. The resulting spectral profiles are processed, reconstructed, and visualized. Computational optical sectioning reconstruction techniques based on a variety of strategies have been demonstrated, including nearest neighbors and iterative deconvolution.

Microscope-based wide field optical spectroscopic systems have the distinct advantage of being able to detect, classify, identify and visualize BWAs down to a single bacterium for instance. These systems boast a spectral resolution on the order of 8 cm$^{-1}$ and a spatial depth resolution of approximately 200 nm with numerical deconvolution methods.

Macroscope-Based System

The wide field macro-spectroscopic system combines in a single platform an illumination subassembly consisting of an illumination source (typically a QTH, Xe, Hg or other metal halide lamp), barrier optical filter(s) and a light-directing module (i.e., direct beam, fiber optic or liquid light guide illumination). An analog color charge-coupled device (CCD) detector is used for ordinary optical and digital image collection. Raman Wavelength selection is done using an imaging or non-imaging spectrometer. The detector is either a room temperature or optionally cooled NIR FPA for NIR image capture or a thermoelectrically cooled (TE) Si CCD detector for UV/visible and fluorescence image capture.

UV, visible or NIR illumination is directed to the sample in a reflected light configuration using a QTH source or other broadband white light source, including metal halide, Hg arc lamps or Xe arc lamps or a transmitted light configuration using QTH or other suitable source through direct illumination, fiber optics or liquid light guides. Light emitted, reflected or transmitted is collected from the sample positioned on the macroscopic sample base through a macro lens.

Ordinary optical imagery of the sample may be obtained using a mirror or beamsplitter or prism arrangement inserted into the collection stack of the macroscope and collecting an image with an analog or digital color or monochrome charge-coupled device (CCD) or CMOS detector. In the Raman spectroscopic mode, the spectroscopic information is obtained via an imaging or non-imaging spectrometer. Also used to complement this can be a focal plane array (FPA) detector (for NIR spectroscopic imaging) or a Si CCD detector (for UV/visible absorption/reflectance, fluorescence and Raman spectroscopic imaging). The NIR FPA is typically comprised of indium gallium arsenide (InGaAs), but may be comprised of other NIR sensitive materials, including platinum silicide (PtSi), indium antimonide (InSb) or mercury cadmium telluride (HgCdTe).

A central processing unit, typically a Pentium computer, is used for spectroscopic data collection and processing. The analog color CCD, NIR FPA and/or Si CCD and liquid crystal imaging spectrometer or other imaging spectrometer (through an appropriate imaging spectrometer controller) are operated with commercial software, such as ChemAcquire (ChemImage Corporation) in conjunction with ChemAnalyze (ChemImage Corporation.).

The use of a macroscopic-based system has the advantage of enabling rapid detection of potential BWAs and CWAs over an even larger area. Previous work has shown the ability image 0.01 mm defects on 200 mm semiconductor wafers using the macroscope system.

Endoscope-Based System

Raman spectroscopy is largely performed in laboratory settings using research-grade light microscope technology as the image-gathering platform. However, Raman spectroscopy is also applicable to in situ industrial process monitoring and in vivo clinical analysis. Both industrial and clinical settings often require compact, lightweight instrumentation suitable for the examination of remote areas that are inaccessible to conventional spectroscopic instrumentation.

A robust wide field spectroscopic system with digital analysis capabilities has been developed. An imaging endoscope integrated with this spectroscopic system provides real-time video inspection capability with spectral analysis. The endoscope couples to a video CCD for real-time video imaging of the analysis area. This allows for quick visual screening of the sample. The endoscope tip has been engineered to filter both laser illumination and collected Raman scatter and fluorescence emission (for Raman and fluorescence applications). The light from the laser delivery fiber is filtered so that only the laser wavelength is presented to the sample. The laser is removed from the collected light so that Raman information is visible to within 200 $cm^{-1}$ of the laser line. The distal end of the Raman endoscope is environmentally resistant and can withstand continuous operation at high temperatures and has been demonstrated to operate from 0–315° C. while maintaining high signal to background (S/B) performance. The distal end can be coupled to a microscope-based system enabling dispersive spectroscopy and spectroscopic imaging to be performed remotely.

The use of an endoscopic-based wide field Raman spectroscopic system has the advantage of being able to detect the presence of suspect BWAs and CWAs in remote locations such as inside a box or envelope.

Ambient Air Sensor System

The ambient air sensor system consists of two parts, a sampling system and a spectroscopic imaging system. The key to the sampling system is the optics block, shown diagrammatically in FIG. 1. This block must support a section of filter medium and provide a complete airtight seal around the periphery of the sampling area. This block must also be easily opened so that either a new filter (discrete filters) or a new section of filter (continuous filters) can be placed in the sampling/optics path.

The sampling system has an inlet, which is open to the atmosphere being tested. Its dimensions are optimized for the sampling flow rate and the anticipated range of particle sizes. For particulate or aerosol sampling, it is important that the inlet have no sharp bends or areas of low linear velocity, which can cause deposition of particulate prior to the collection filter. The sampling system also has a sampling pump, providing the vacuum to pull ambient air through the filter. Anticipated flow rates are in the 0.5 to 2.0 L/min range, and the expected vacuum is in the 100 in.-$H_2O$ (180 mm-Hg) range.

The sampling system is typically not run continuously but rather in a series of discrete sampling periods. At the end of each period, it might be necessary to replace the filter medium. This can be done either by the operator or automatically. For continuous sampling, the filter medium can be in a tape-like configuration and new samples of filter can be positioned in the optics block by a tape-drive mechanism, similar to that of an audiocassette.

Once the particulates have been trapped on the filter medium, wide field spectroscopy is used to detect and classify the BWA or CWA present. If the excitation source is a laser, coupled to the optics block using conventional or fiber optics, whose light is evenly distributed over the whole sampling area, Raman imaging can be used. In another configuration, a light source comprised of a broadband UV/Vis, filtered UV/Vis, or a UV/Vis laser can be used to excite autofluorescence. The imaging detector can be of the liquid crystal tunable type or another imaging spectrometer type as described earlier and a CCD or other array camera can be used to image the sampling area at multiple wavelengths. Coupling of the detector to the optics block can be through fiber-based or conventional optics. The detector data is processed using chemometric and image analysis tools such as those found in the ChemAnalyze software (ChemImage Corporation).

The typical operating mode of this type of ambient air monitor is usually as a series of sampling periods during which periodic spectroscopic image measurements are taken. The results from the previous and current sampling periods are interpreted by a system computer which can display results and activate warning and danger alarms, or initiate some action such as turning off a building outside air intake.

Handheld Biothreat Detector

Current spectroscopy based biothreat detection systems are limited in size and weight by the individual components required to produce and focus the illumination, collect the emitted or scattered light as well as perform the required spectral analysis. One of the advantages of the wide field method of detection of pathogenic microorganisms is the simplicity this method permits in the design, layout and integration of the excitation and detection systems.

The functional and configurational requirements of this method will allow several miniaturizable components to be implemented without significant performance degradation or limitations. For example, a low cost compact spectrometer comprised of a wavelength tunable filter or MOEMS fabricated wavelength dispersive elements can be designed and fabricated with sufficient resolution to detect the spectral components emitted from the specimen being investigated. Advances in active pixel CMOS CCD detectors or avalanche photo diodes will similarly enable small compact sensors to detect and spatially resolve the resulting spectral features. The effective use of such scalable optical elements with this wide field method makes it feasible to scale down the overall size and weight of such a detection system thereby enabling a portable handheld unit.

Results

Spectra generated using traditional spectroscopic methods can potentially reveal a wealth of information about molecular properties of BWAs and CWAs. Wide field spectroscopy as presented here makes this practical and reliable, even allowing detection down to a single bacterium if necessary. This also allows us to characterize bacteria spores in the presence of non-threatening 'masking' agents and represents a critical issue in the detection and identification of BWAs and CWAs. Difficulties exist when trying to differentiate spores from different bacterial species. FIG. 2 shows dispersive wide field Raman spectra of three different bacterial spores types. Despite the genetic and morphological similarities, wide field Raman spectroscopy has been used to sufficiently discriminate among the different bacteria spores.

Figure 3A:
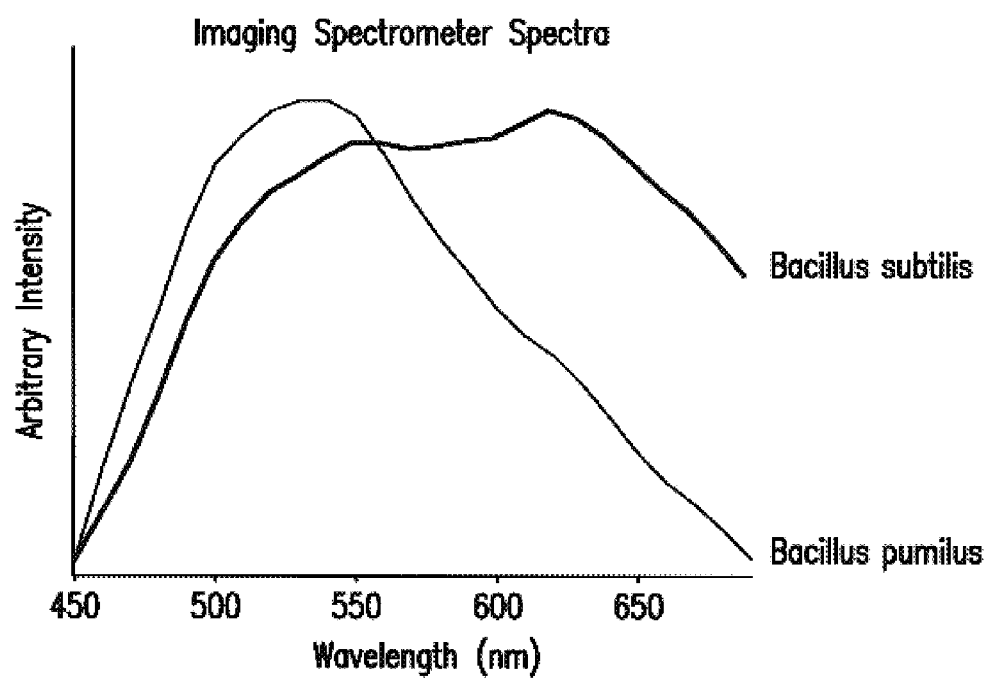
FIG. 3 is micro imaging field fluorescence-spectroscopy of two different bacterial spore types.
Figure 3B:
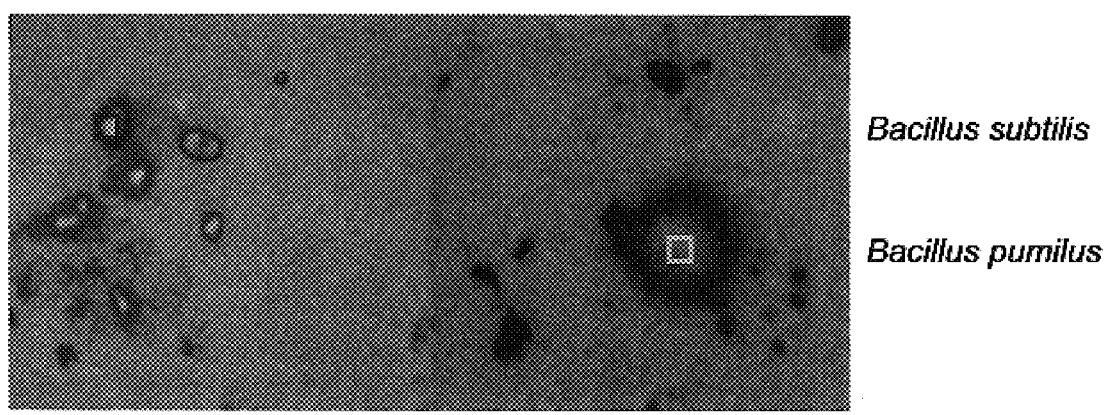

FIG. 3 shows how wide field fluorescence spectroscopic imaging obtained thru an imaging spectrometer can be used to distinguish between bacteria spore types. The fluorescence spectra in the lower portion of the figure were obtained from the color-coded boxed regions in the concatenated fluorescence spectroscopic images above. It can be seen that *Bacillus subtilis* spores and *Bacillus pumilus* spores exhibit fluorescence peaks maxima at 540 nm and 630 nm, respectively.

FIG. 4 shows the results of rapid wide field spectroscopic examination of unidentified samples supplied by the US Armed Forces Institute of Pathology (AFIP). These samples include 4 samples comprising 6 unknown powders and a sample of BG spores.

FIG. 4A shows wide field Raman spectra (green laser excitation) of the 6 unidentified powders through the vials.

FIG. 4B shows wide field Raman spectra (red laser excitation) of the 6 unidentified powders.

Figures 1, 4D:
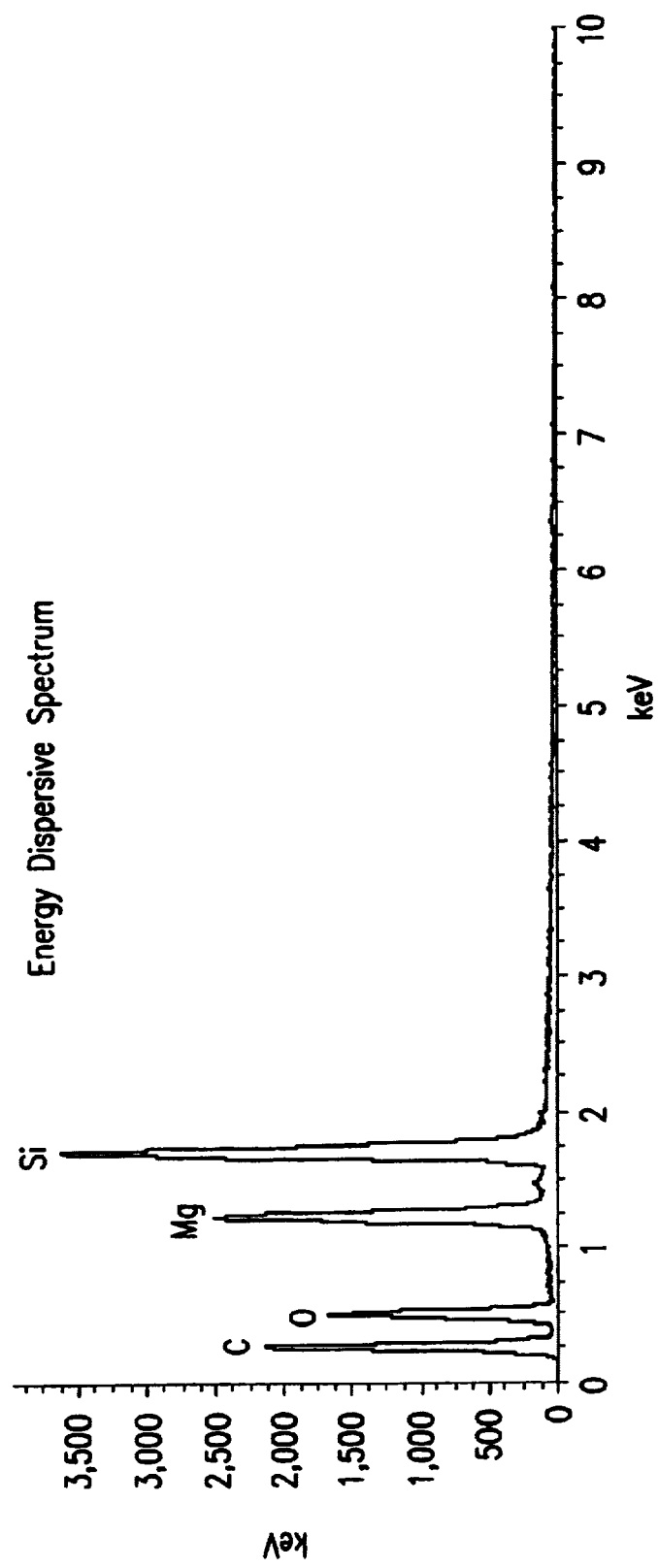
Figures 2, 4D:
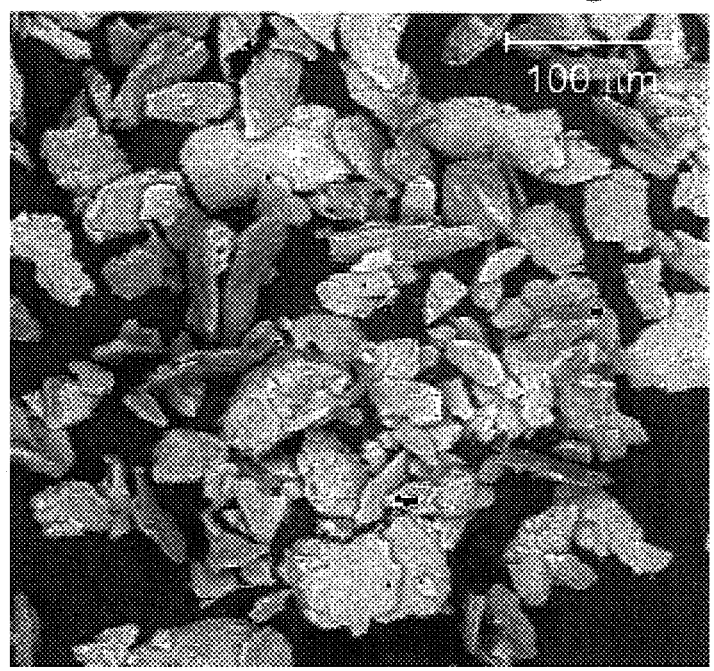

FIGS. 4C–4D (Sample 1331-002) show wide field Raman, IR and SEM-EDS results on a first of the 6 unidentified powders. The sample is inorganic and most likely talc.

Figures 1, 4F:
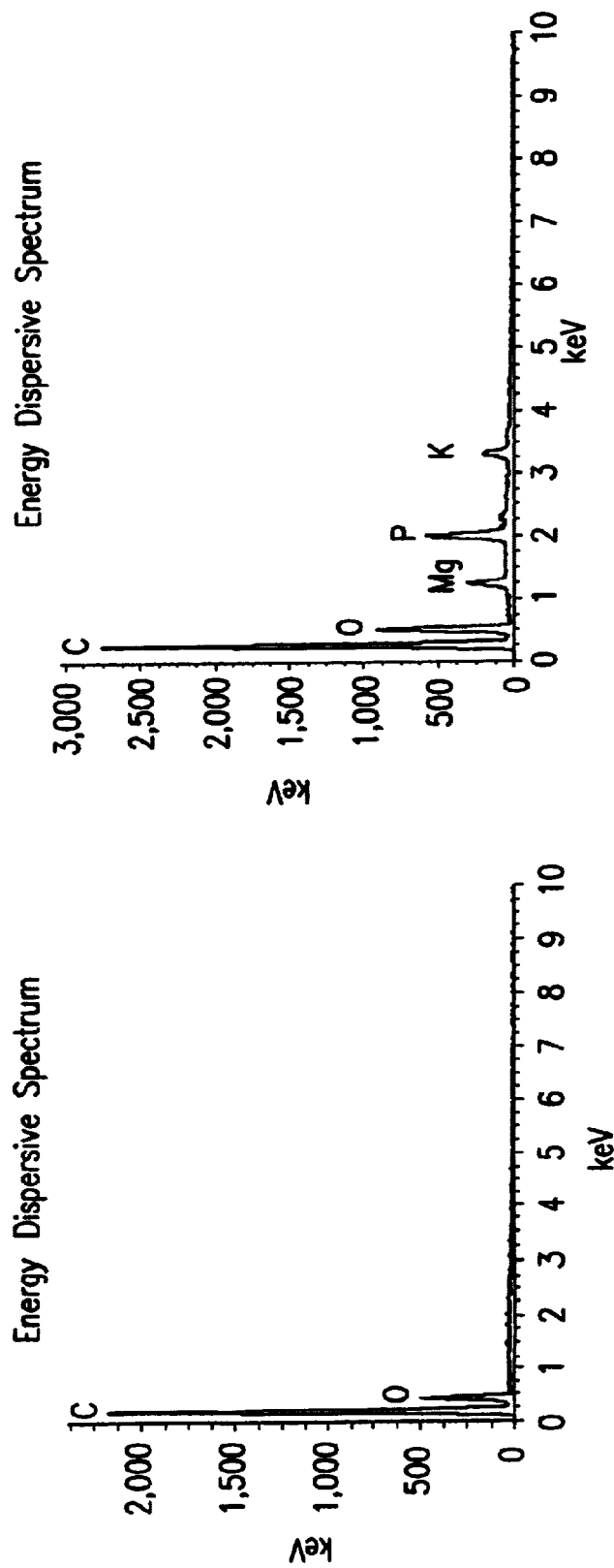
Figures 2, 4F:
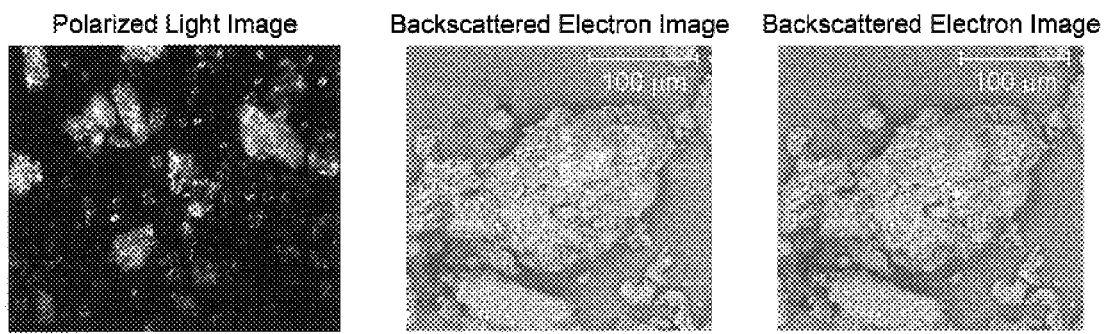

FIGS. 4E–4F (Sample 1325-002) show wide field Raman, IR and SEM-EDS results on a second of the 6 unidentified samples. The sample is organic and most likely starch, possibly corn starch.

Figures 1, 4H:
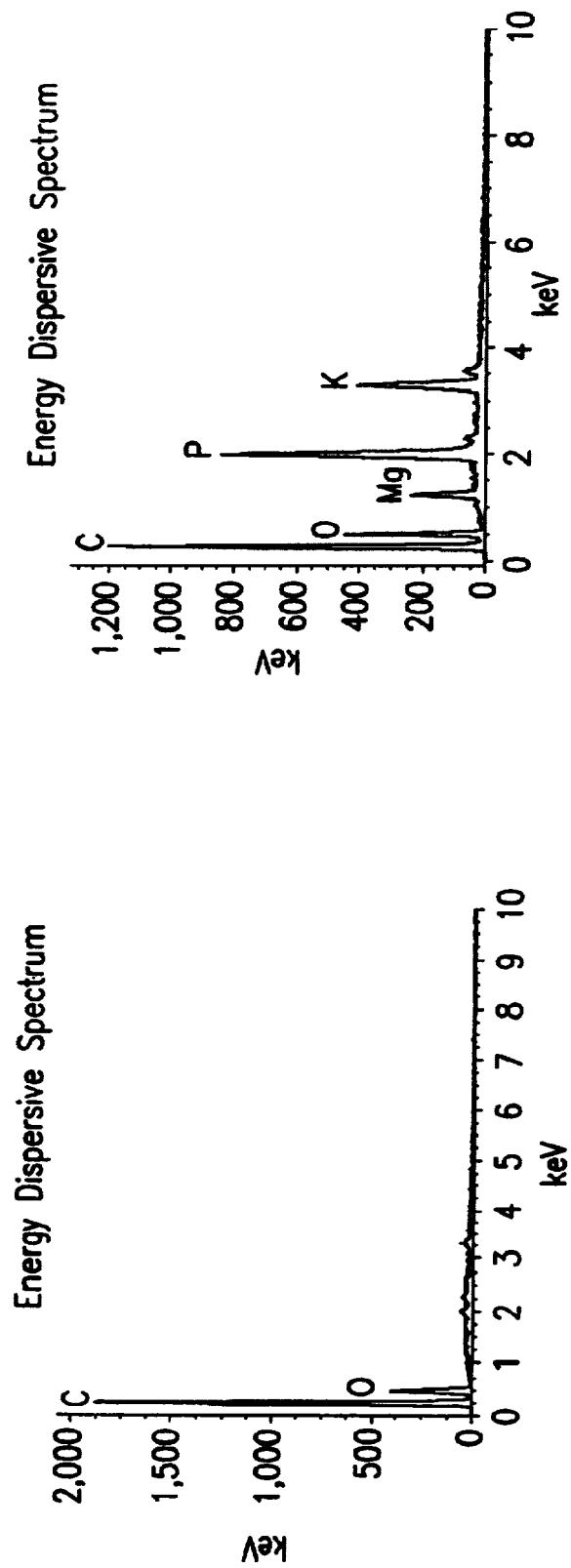
Figures 2, 4H:
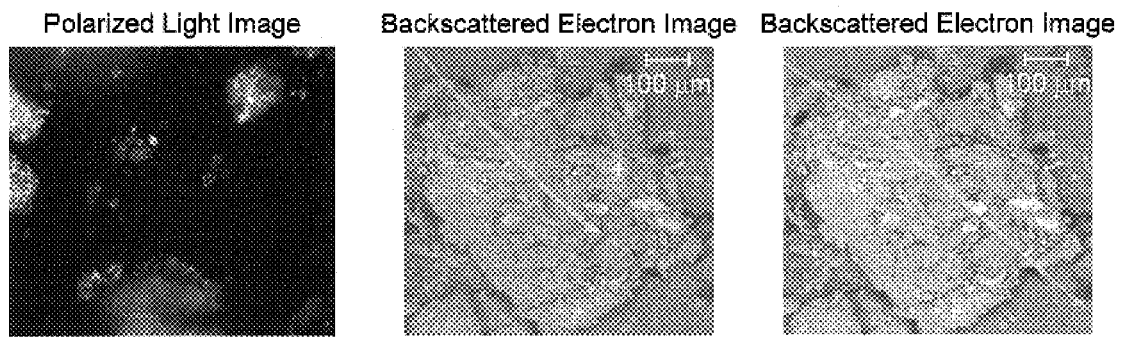
Figure 4I:
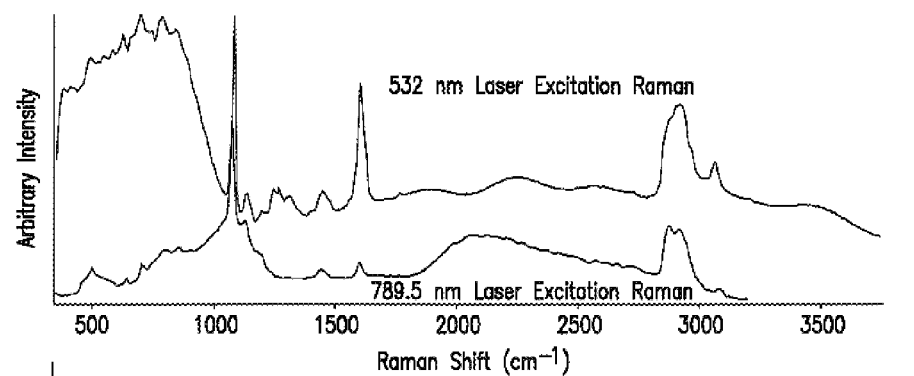
FIGS. 4I–4N (Sample 1291-006) show dispersive Raman, IR and SEM-EDS results on the remaining unidentified powders. There are 3 distinct types of powders in this sample. All 3 have organic content, while 2 of the 3 are fairly rich in aluminosilicates. One of the powders is likely a complex aromatic hydrocarbon.
Figure 1:
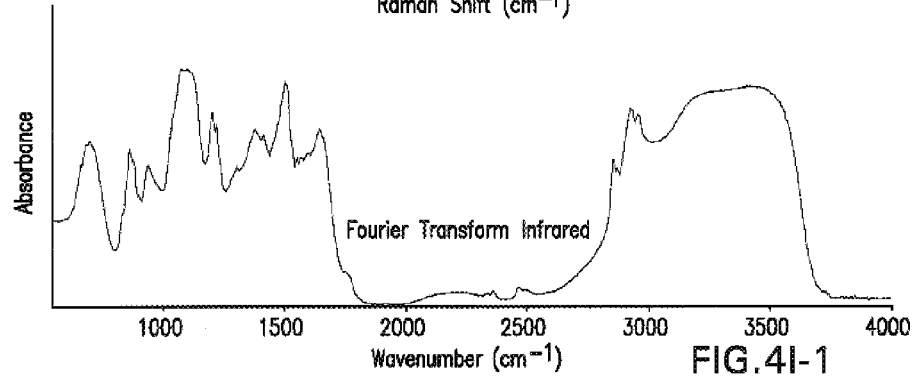
FIG. 1 is a schematic of an ambient air BWA and CWA sensor based on optical spectroscopic detection.
Figure 2:
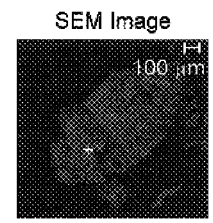
Figures 1, 4J:
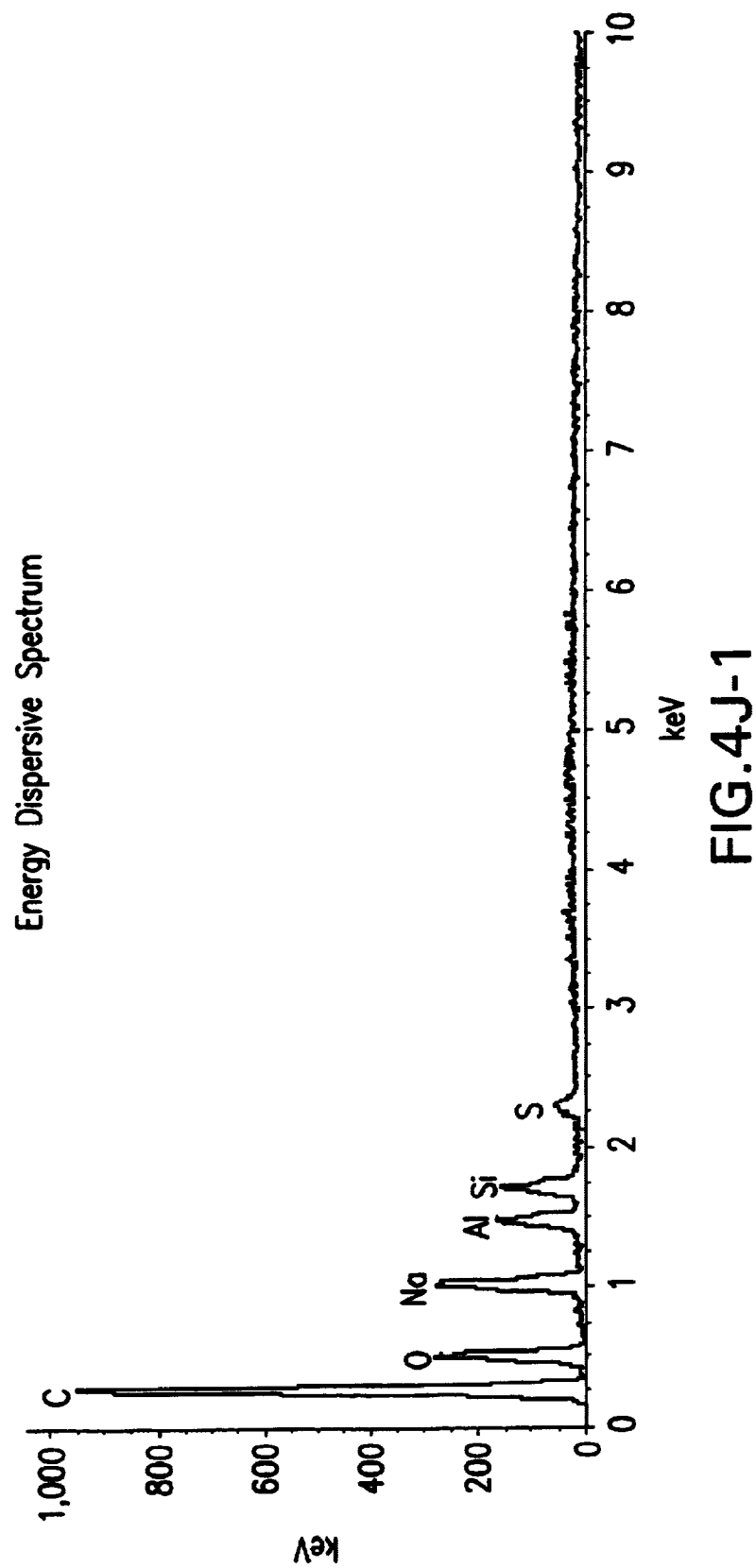
Figures 2, 4J:
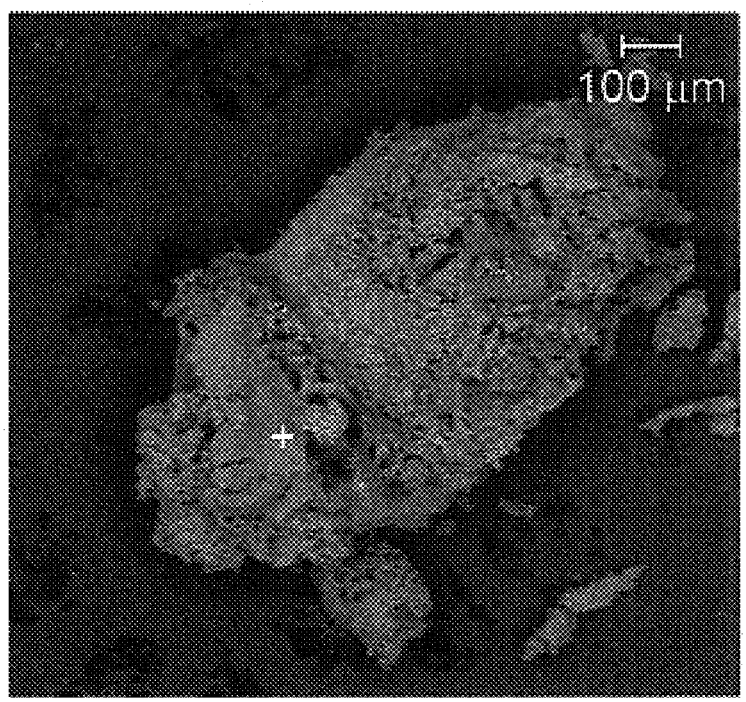
Figure 4K:
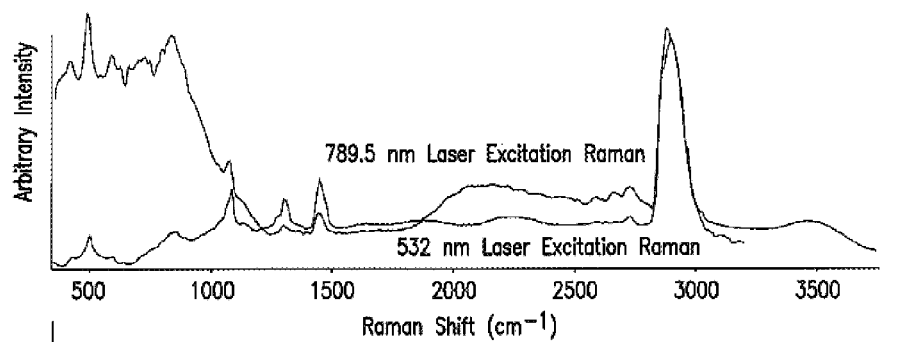
Figure 1:
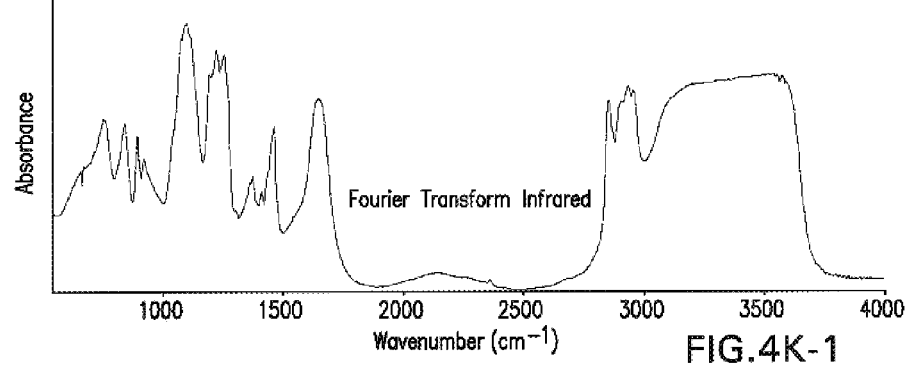
Figure 2:
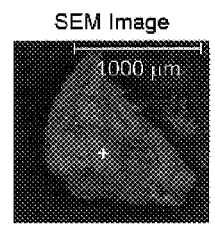
Figures 1, 4L:
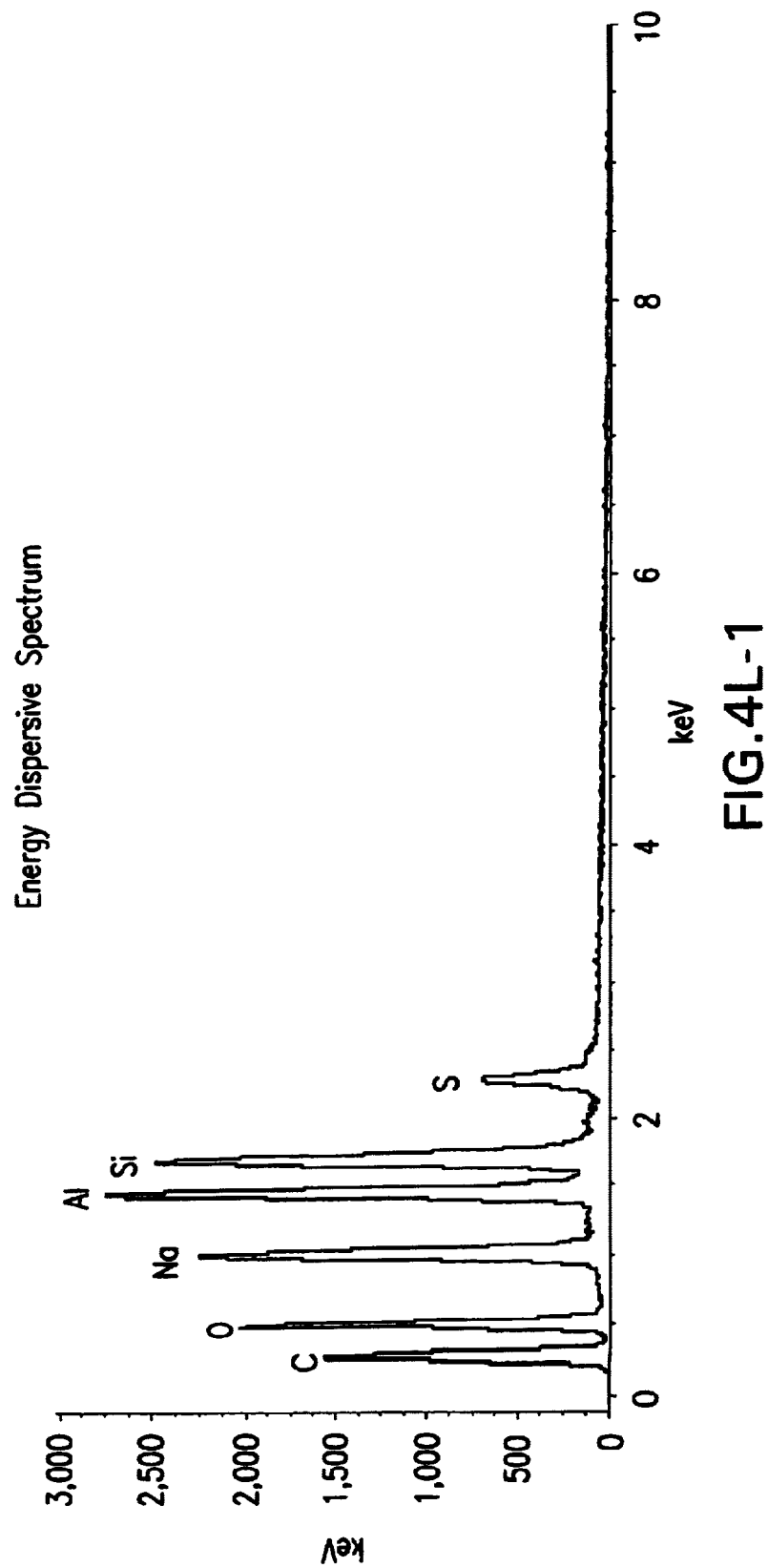
Figures 2, 4L:
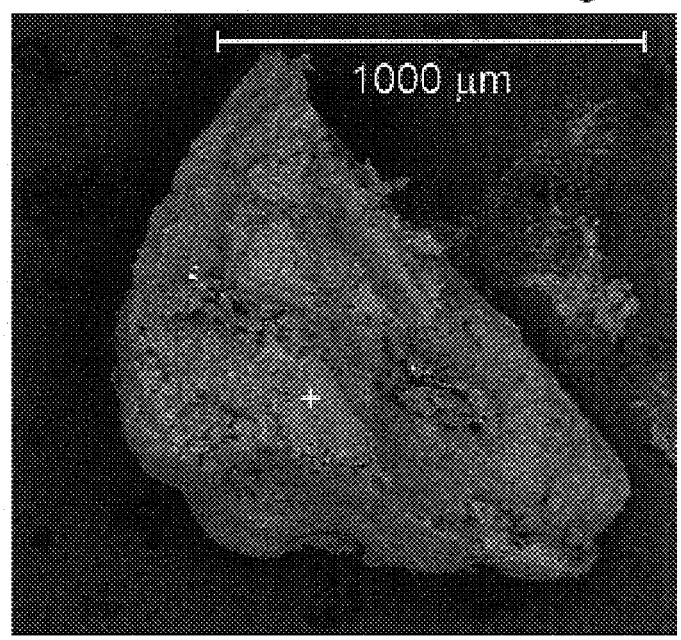
Figure 4M:
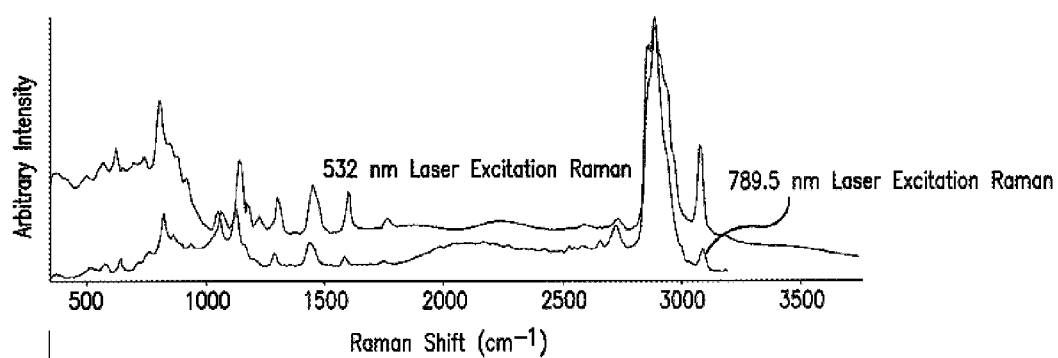
Figure 1:
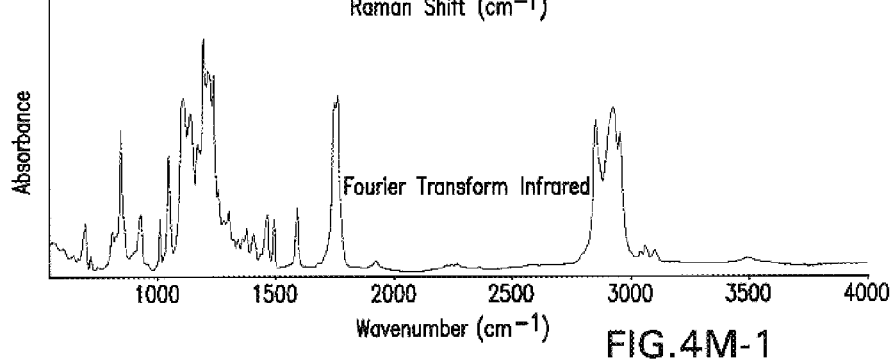
Figure 2:
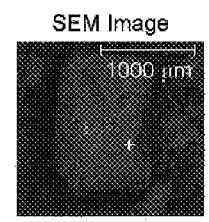
Figures 1, 4N:
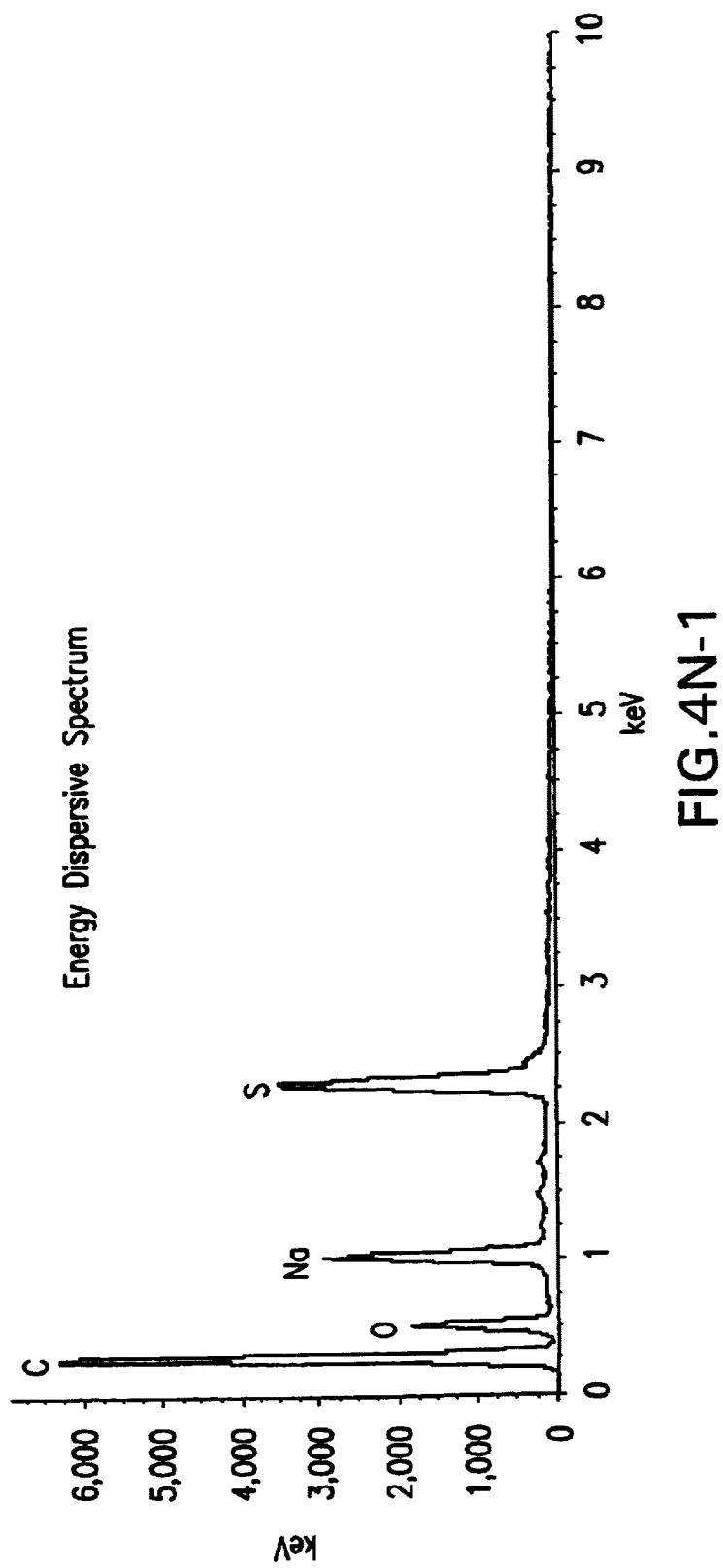
Figures 2, 4N:
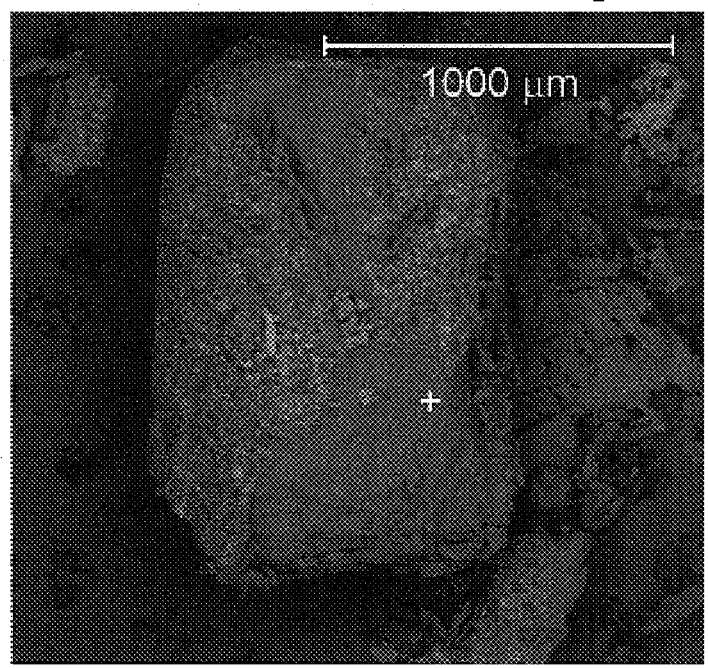

FIGS. 4G–4H (Sample 1303-002) show wide field Raman, IR and SEM-EDS results on a third of the 6 unidentified powders. The sample is organic and most likely starch, possibly corn starch.

FIGS. 4I–4N (Sample 1291-006) show wide field Raman, IR and SEM-EDS results on the remaining unidentified powders. There are 3 distinct types of powders in this sample. All 3 have organic content, while 2 of the 3 are fairly rich in aluminosilicates. One of the powders is likely a complex aromatic hydrocarbon.

FIG. 4O show wide filed Raman spectra and images of 2 common white powders that can easily be differentiated with Raman Chemical Imaging.

Figure 4P:
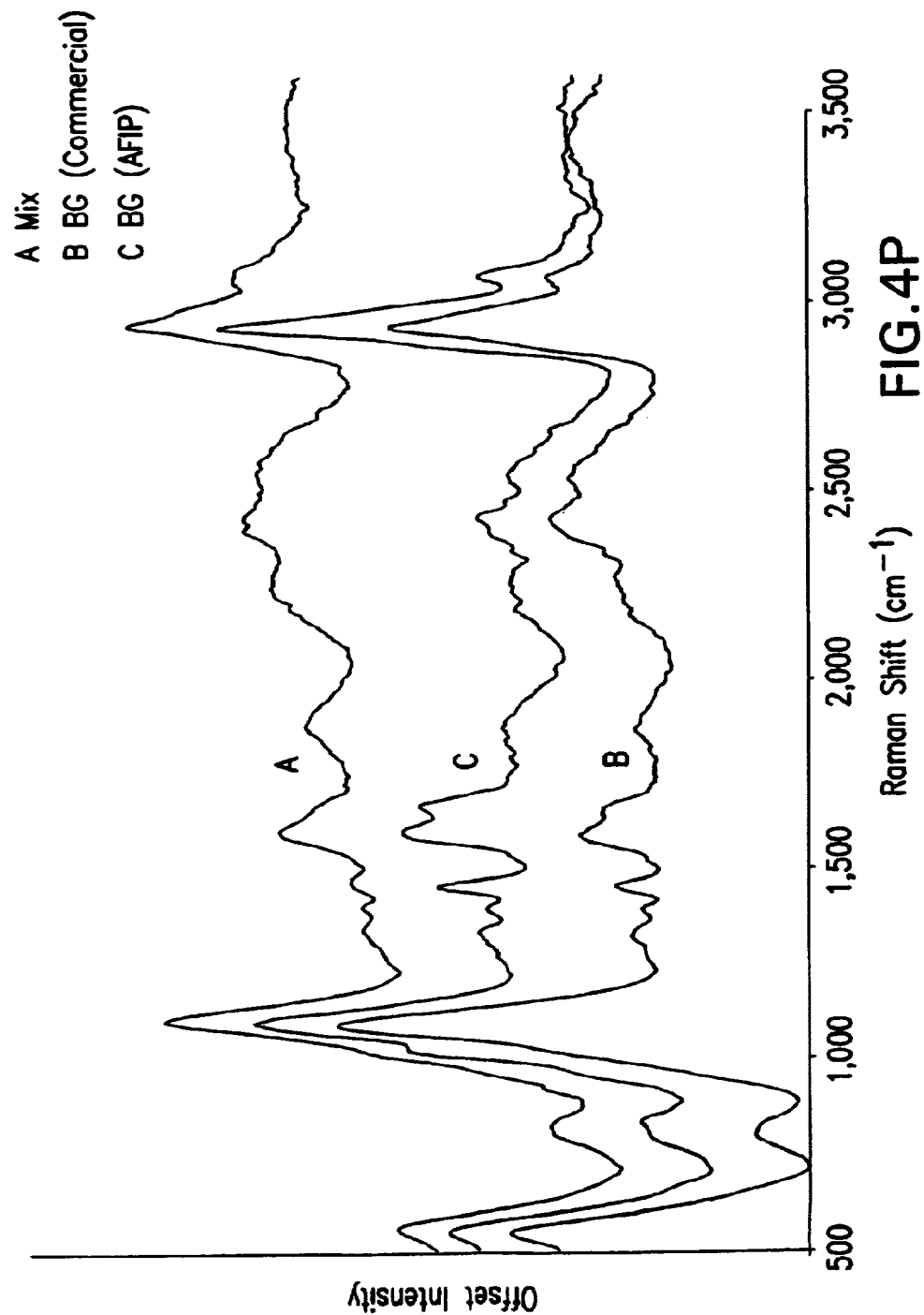
FIG. 4P shows the differences in Raman spectra of various Bacillus spores.

FIG. 4P shows wide field Raman spectra of sample BG spores compared with commercially available BG spores. A Raman spectrum of a mixture of the 2 samples is shown, as well. Raman indicates the samples are similar, almost identical.

Figures 1, 4Q:
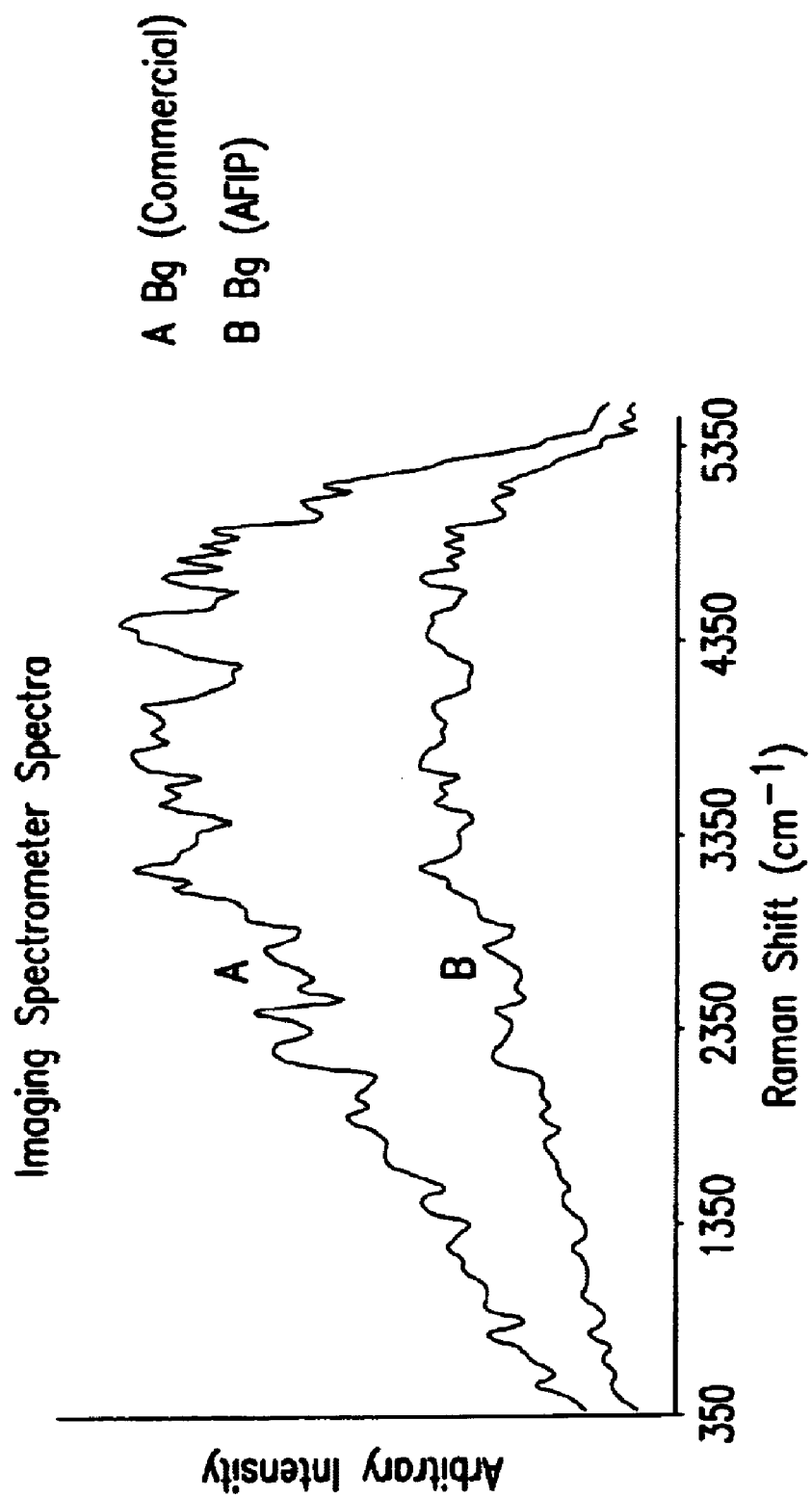
Figures 2, 4Q:
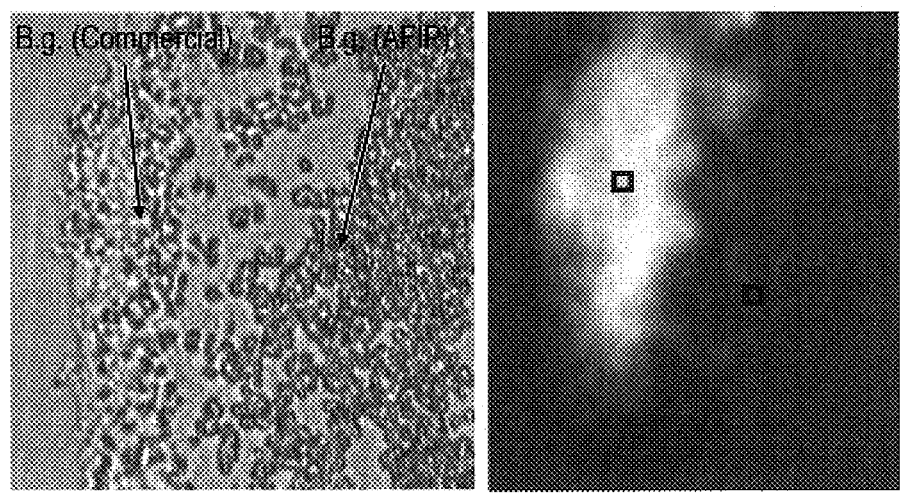

FIG. 4Q shows a wide field Raman Image where the 2 similar spores are differentiated on the basis of autofluorescence differences.

FIG. 5 shows the results from additional spore samples selected specifically because the inherent difficulty in differentiating these species. They include *Bacillus thuriengensis* (BT), *Bacillus cereus* (BC) and BG. The wide field Raman spectra from the 3 spores are different. These differences suggest a good chance of differentiating anthrax from non-threats. The details follow:

FIG. 5A shows raw wide field Raman spectra of BT and the suspension residue. The residue is from the suspension liquid.

FIG. 5B shows background corrected wide field spectra of BT and residue. Both the spores spectrum and residue spectrum have been divided by a spectrum of the microscope slide.

Figure 5C:
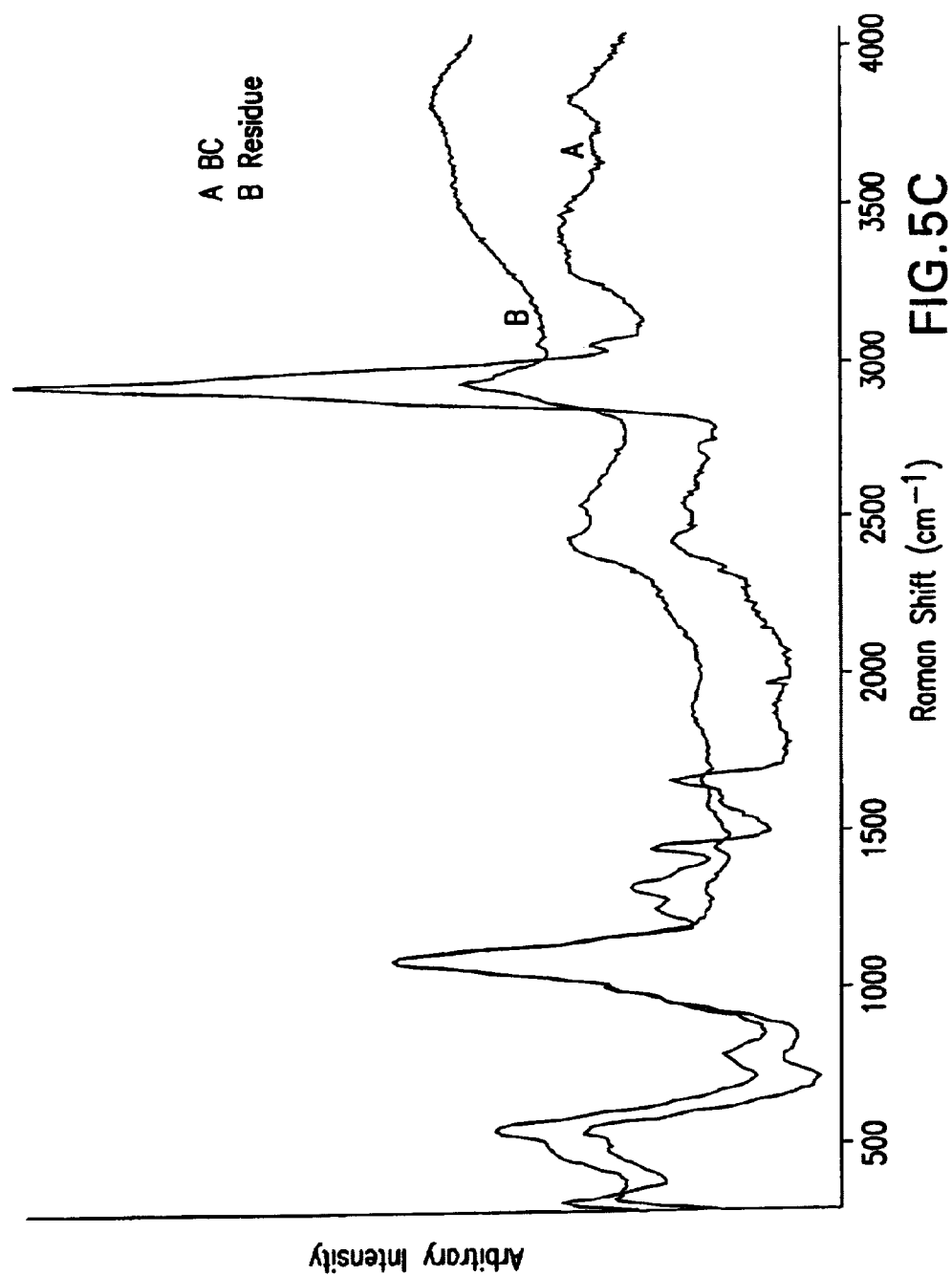

FIG. 5C shows raw Raman spectra of BC and the suspension residue.

FIG. 5D shows background corrected spectra of BC and residue FIG. 5E shows a compilation of sample BT, BC and BG spectra with microscope slide background correction. The spectra are different. The differences are greatest in the fingerprint region.

Figure 5F:
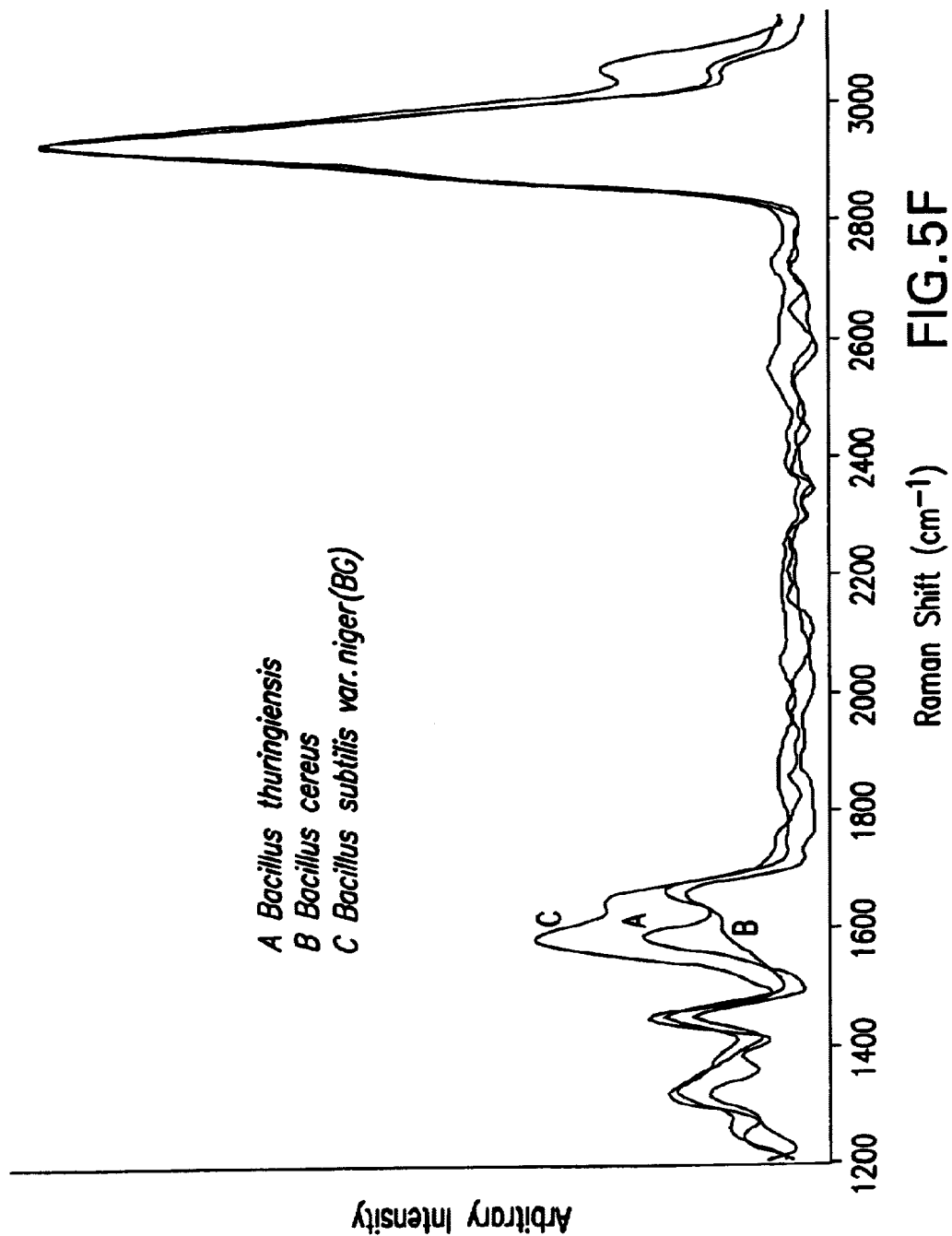

FIG. 5F shows a compilation of the 3 spores after baseline subtraction and normalization to the CH region spectral feature (~2950 cm$^{-1}$).

FIG. 6 shows how wide field Raman spectroscopy can be applied to distinguish between multiple bacterial strains within a single species.

Figure 7:
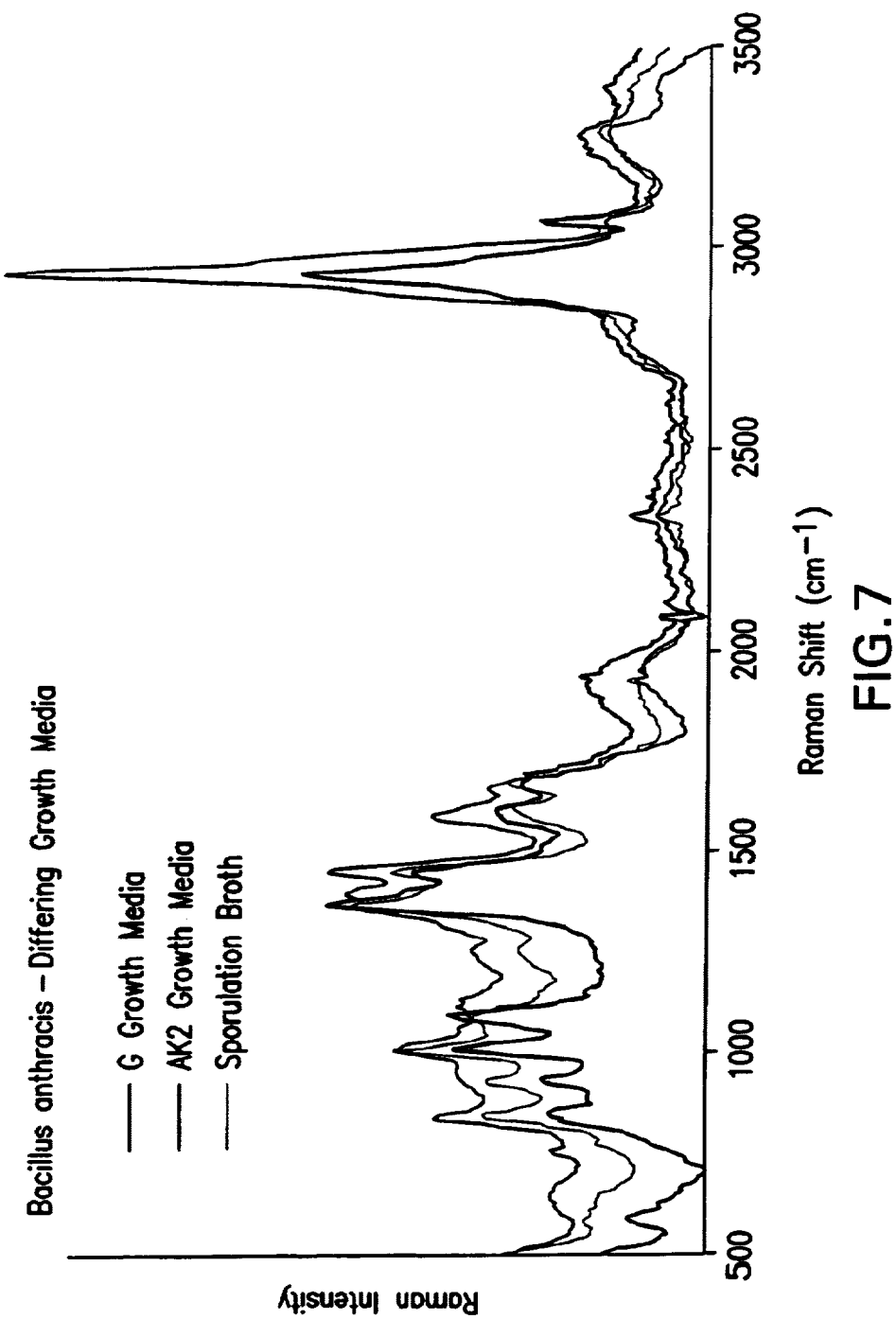
FIG. 7 shows how Raman spectra can be applied to distinguish between the same species and strain of bacteria grown under differing conditions.

FIG. 7 shows how wide field Raman spectroscopy can be applied to distinguish between the same species and strain of bacteria grown under differing conditions.

Figure 8B:
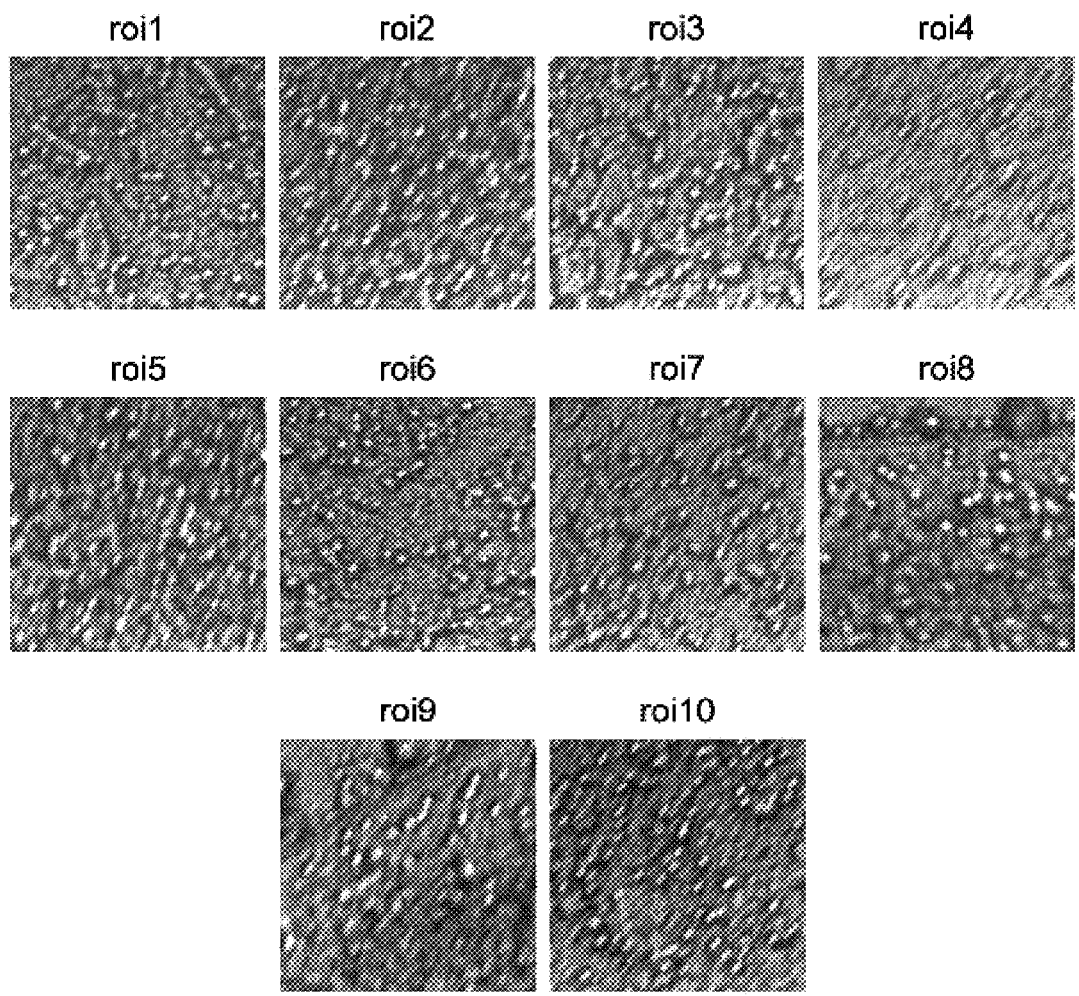
FIG. 8 shows the reproducibility of measurements of different regions of *anthracis* (Anthrax) spores

FIG. 8 shows wide field Raman spectroscopy of various regions of interest of *Bacillus anthracis* (Anthrax) spores and the ability to reproducibly distinguish between similar materials.

FIG. 9 shows how wide field Raman Spectroscopy can be applied to distinguish between viable and non-viable endospores, a critical variable in determining real threat level.

Figure 10A:
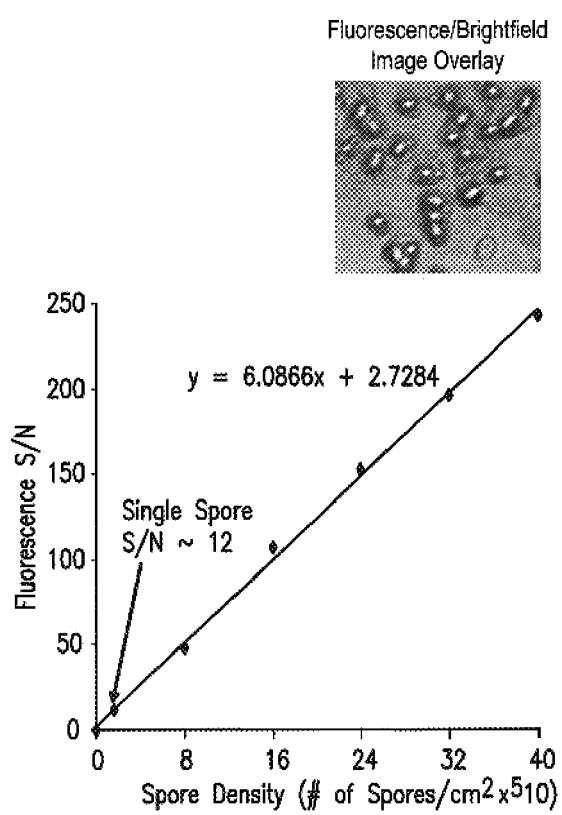
FIG. 10 shows the S/N obtained in Fluorescence or Raman spectral detection using this wide field method. This quantifies the ability to detect microorganisms in low concentrations.
Figure 10B:
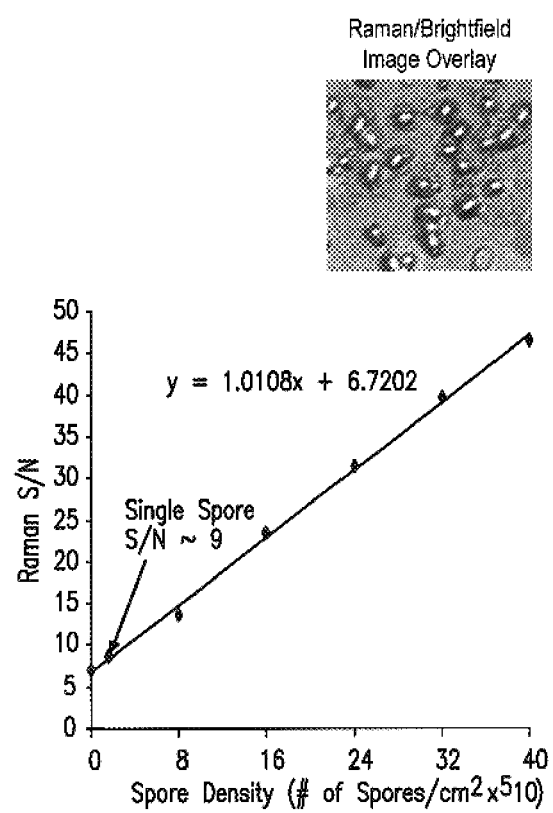

FIG. 10 shows the wide field Fluorescence and Raman signal to noise as a function of spores present and the overall sensitivity of this method.

Figure 11:
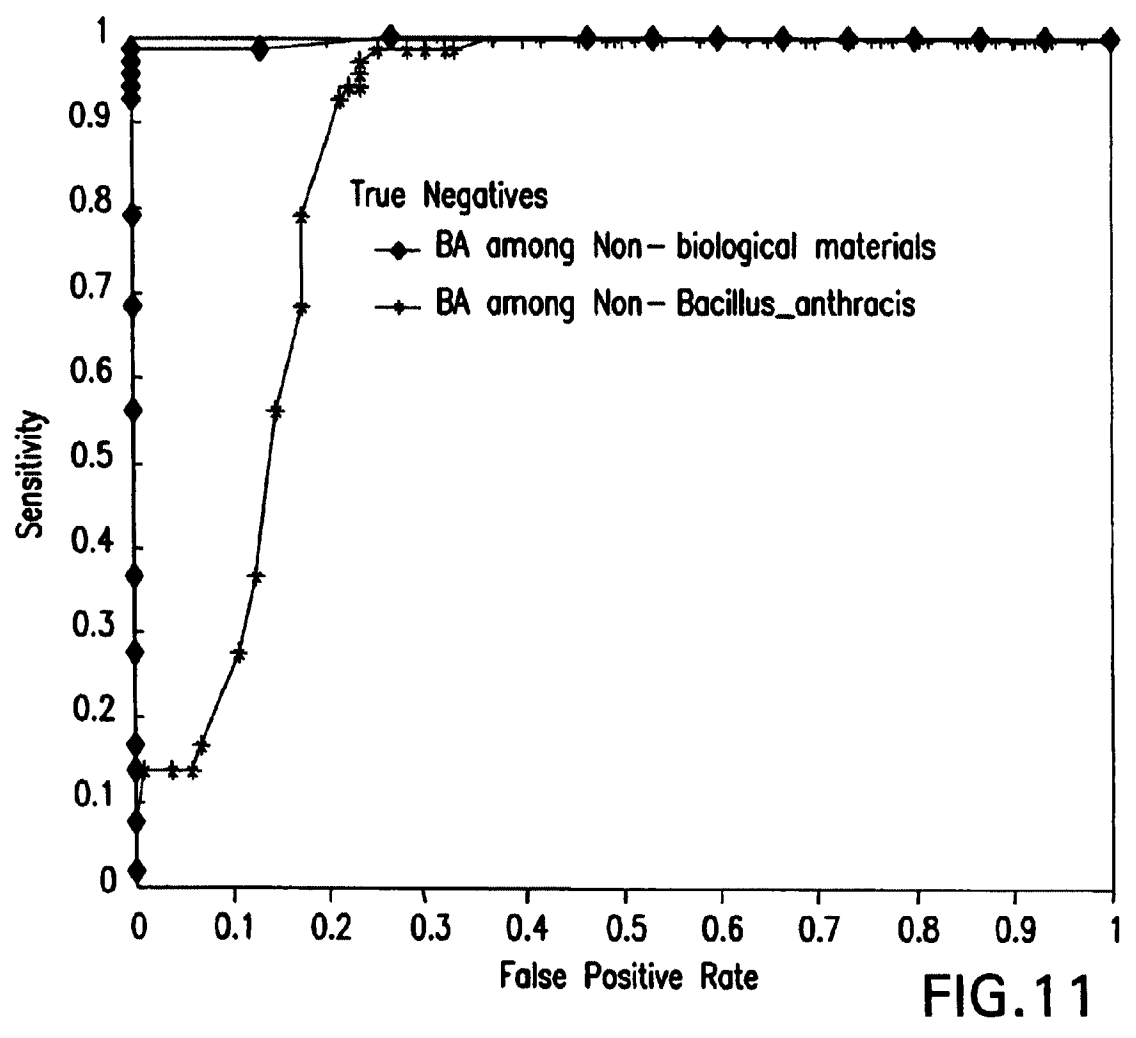

FIG. 11 shows a ROC analysis of the wide field Raman spectroscopic results showing the specificity of this method to distinguish anthrax from other simulants.

Figure 12A:
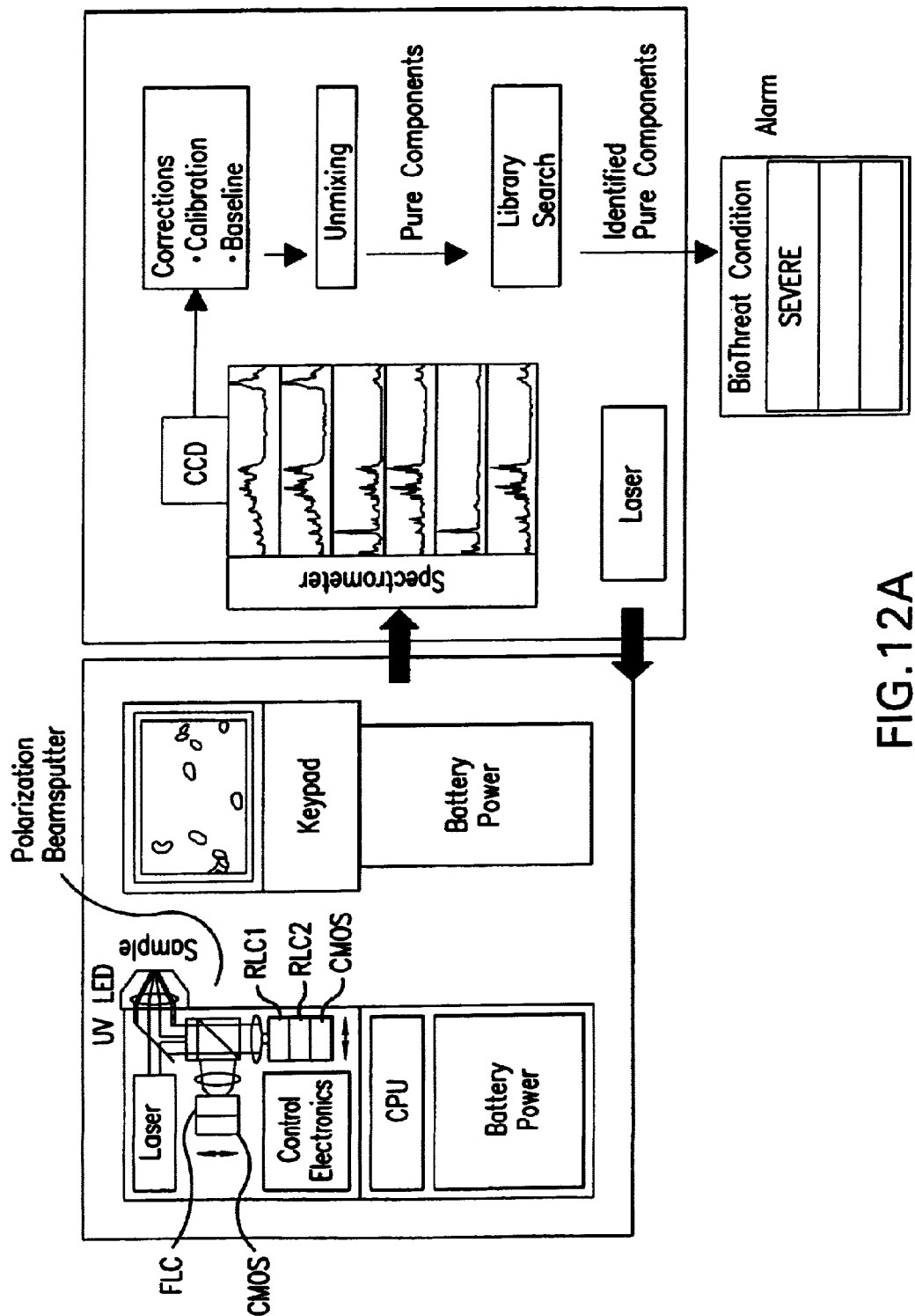
FIG. 12 shows a handheld pathogenic microorganism detection unit that is based on the wide field Raman method of the present invention.
Figure 12B:
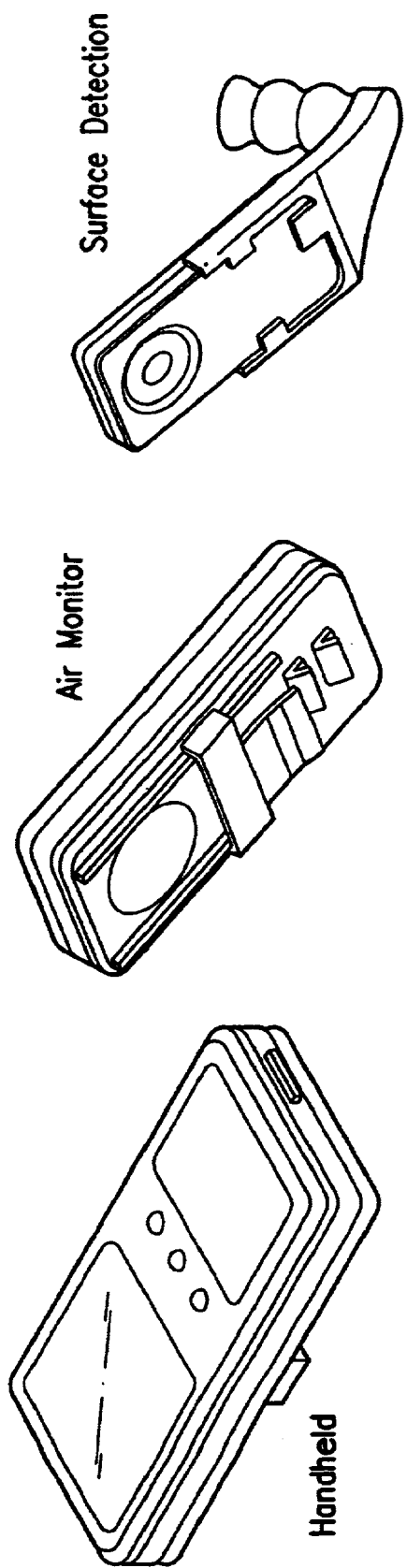

FIG. 12 shows a handheld pathogenic microorganism detection unit which measures approximately 6"×3"×1" and is based on the wide field Raman method. This particular unit has stacked or modular functional layers that consist of the top layer containing the display and user interface, the middle layer housing the illuminator, spectrometer, sensor and control electronics as well as a lower layer that holds a sampling module. Each layer can be changed to meet specific needs or functional requirements. For example, the sampling module would differ for sampling pathogens in different environments and is shown for either ambient air monitoring or surface detection modes. This lower sampling module can also be exchanged for another to sample pathogens in various fluids, such as water or blood.

Anthrax spores have been used for wide field Raman in a secure biohazard laboratory (FIG. 8). Different strains of Anthrax spores have been differentiated by the wide field Raman method (FIG. 6). Additionally, wide field Raman spectroscopy has been used to differentiate the same species and strain grown under different environmental conditions and/or growth medium (FIG. 7). This ability can have useful investigatory applications. And, wide field Raman spectroscopy has been used to differentiate viable from non-viable endospores (FIG. 9). Viability of suspect spores is a critical variable in determining the real threat posed.

The inventors anticipate that the following pathogenic microorganisms will be susceptible to detection and classification as to species, strains, and viability by the wide field Raman method and resulting spectral profile: cryptosporidia; *Escherichia coli*; Plague (*Yersinia pestis*; Smallpox (variola major); Tularemia (*Francisella tularensis; Brucellosis (Brucella* species; *Clostridium perfringens*; Glanders (*Burkholderia mallei*; Melioidosis (*Burkholderia pseudomallei*; Psittacosis (*Chlamydia psittaci*; Q fever (*Coxiella burnetii*; Typhus fever (*Rickettsia prowazekii; Vibrio; Giardia; Candida albicans; Enterococcus faecalis; Staphylococcus epidermidis; Staphylococcus aureus; Enterobacter aerogenes; Corynebacterium diphtheriae; Pseudomonas aeruginosa; Acinetobacter calcoaceticus; Klebsiella pneumoniae; Serratia marcescens*; filoviruses (such as Ebola and Marburg viruses), naviruses (such as Lassa fever and Machupo viruses) and alphaviruses (such as Venezuelan equine encephalitis, eastern equine encephalitis, and western equine encephalitis).

Advanced spectral analysis and chemometric tools take these differences in Raman or fluorescence spectra to perform a identification of species, as in FIG. 11. Similar approaches can be applied to create an image by taking sequentially acquired spectra from at least two different regions of the surface of the substrate under investigation. The following is a representative algorithm for performing such an analysis:

1) Divide the raw image by a background image (taken without the sample)
2) Do cosmic filtering on the resultant image (median filtering for pixels whose value differs significantly from the mean of a local neighborhood)
3) Use an alignment procedure to correct for slight movements of the sample during data collection 4) Apply a spatial average filter 5) Perform a spectral normalization (helps correct for varying illumination across the sample)
6) Perform a spectral running average over each set of three spectral points
7) Extract a set of frames corresponding to 550 to 620 nm. The spectra for both bacterial spores (*Bacillus subtilis* var *niger* and *Bacillus pumilus*) are essentially linear over this range. *Bacillus subtilis* var *niger* has a positive slope and *Bacillus pumilus* has a negative slope.
8) Create a single frame image in which each intensity value is the slope of the spectral sub-region (from the last image). The slope is determined via a least-squares fit.
9) Scale the resulting image between 0 and 4095. Keep track of the point from 0 to 4095 that corresponds to 0 in the prior image (the "Zero point").
10) Create a mask image from a series of steps:
    a) From the aligned image ($3^{rd}$ step), calculate a single frame "brightest" image in which the intensity of each pixel is the maximum intensity value for each spectrum.
    b) Scale this brightest image between 0 and 4095.
    c) Create a binarized image from the scaled image, in which every pixel whose intensity is greater than 900 is set to 1 in the new image and every pixel whose intensity is less than 900 is set to 0 in the new image. The value of 900 was chosen by an examination of the histogram associated with the scaled image. A future improvement to the algorithm would be to automatically select the threshold by numerically analyzing the histogram for a given image.
11) Multiply the scaled image from step 9 by the mask image from step 10. This restricts the visual display to only areas that correspond to spores. The result is a gray scale image in which intensity values below the zero point defined in step 9 correspond to *bacillus pumilus* and the intensity values above the zero point correspond to *bacillus subtilis* var *niger*.
12) The final RGB image is then created by setting all the "negative" values to red and all the "positive" values to green.

Applications

There is a great need for a spectroscopic and digital analysis systems that can provide high throughput, non-contact, real-time detection, classification and identification of BWAs and CWAs with high accuracy and with limited or no sample preparation required. The user base for an instrument suitable for objective assessment of BWAs and CWAs will consist of hazardous materials (HAZMAT) teams, government and private facilities where potential threats are high, mail handling facilities, academic, industrial and medical research laboratories, etc.

The benefits to the target users of an instantaneous Anthrax or other microorganism threat detection system will be substantial. Configured in the macroscopic version of the technology, spectroscopic imaging can be employed for rapid assessment of large areas for suspect BWAs and CWAs based on their fluorescence, NIR and/or UV/visible response. Configured in the microscopic mode, positive detection, classification, identification and visualization of suspect BWAs and CWAs can be made. Configured in the endoscopic mode, BWAs and CWAs can be detected, classified, identified and visualized remotely. Configured in FAST mode, BWAs and CWAs can be detected, classified, identified and visualized remotely or at the microscope in real-time. When configured as an air sampler, unambiguous detection of BWAs and CWAs can be done.

When performed in combination the effectiveness of characterizing BWAs and CWAs will likely be enhanced. Benefits will include, but are not limited to, the following:
   Rapid large area scanning to detect suspect BWAs and CWAs.
   Positive detection, classification, identification and visualization of suspect BWAs and CWAs.
   Non-contact
   Limited or no sample preparation required.
   Remote detection, classification, identification and visualization of suspect BWAs and CWAs.
   Real-time detection, classification, identification and visualization of suspect BWAs and CWAs in solid or gaseous samples.

Specific applications of a wide field imaging and spectroscopic system for instantaneous Anthrax detection will include the following:
   Discrimination of threatening and non-threatening 'masking' agents
   Spatial distribution of BWAs and CWAs
   Spatial distribution of BWAs and CWAs down to single bacterial spores.

Advantages Over Currently Available Technology

Traditional approaches to detection of BWAs and CWAs include inoculation methods, enzyme-linked immunosorbent assay (ELISA) methods, BioThreat Alert (BTA) test strips, DNA-based tests, DNA chip analyses and mass spectrometry. Inoculation methods involve the inoculation of suspect culture or specimen into an animal that is then observed for development of disease. In addition to animal cruelty issues, there are drawbacks with this approach including the extensive amount of time required to reach a point of detection.

ELISA tests involve antibody detection. This technique is also slow and suffers from high false positive (unrelated antibody reacts with antigen nonspecifically) and worse, high false negatives (interfering compounds present in blood or antibodies not concentrated enough to be detected). Furthermore, a patient can test positive to antibodies long after the patient has recovered.

BTA test strips are small plastic devices that work very much like a home pregnancy test. The test strips contain specific antibodies that change color on the strip indicating the presence of a bio-threat agent. A negative result means the bio-threat agent is not present within the detection limit of the strip. Although results can be obtained in a relatively short period (15 minutes), the incidence of false negatives and false positives is high.

DNA-based tests detect agents by recognizing their genetic sequences. While more sensitive than BTA test strips, DNA-based tests are susceptible to masking agents and involve a lengthy analysis time. DNA chip analysis involves the immobilization of DNA strands on a Si or glass wafer chip. DNA will bind to or hybridize complementary DNA strands in the sample being tested. A specially designed microscope detects where the DNA hybridize.

Amplification is achieved by polymerase chain reaction (PCR). Detection of bio-threat agent is reported to be possible within minutes.

The limitations of DNA-based methods are two-fold. First, DNA methods are designed to detect a specific bio-threat agent through its unique DNA sequences. Therefore, each DNA test is specific to one agent and if it is desired to detect additional agents, additional test reagents must be developed. A second limitation revolves to the problems of false negatives and false positives due to environmental contamination. DNA tests are well known to have problems yielding correct results in "real-world" samples.

Mass Spectrometry (MS) uses the pattern of mass fragments when a cell or spore is subjected to an ionization process under high vacuum to characterize organisms. It has the advantage of very sensitive detection but requires a sophisticated sampling system in order to deliver a representative sample to the ionizer. The main limitation of MS is that it requires the use of high vacuum pumps that are inherently delicate and expensive. An additional limitation is that it is a destructive technique, in contrast to Spectroscopic Chemical Imaging, which is a completely no-destructive technique.

Alternative technologies/opportunities include microprobes or microscopes based on micro-spectroscopic methods including Raman, fluorescence, NIR, etc. for rapid, non-contact and accurate detection of BWAs and CWAs. These types of tools offer the potential to detect, classify, identify and visualize the distribution of BWAs and CWAs in the presence of other BWAs, CWAs and/or non-threatening 'masking' agents in either a local or remote environment—characteristics that no traditional method can provide. Such tools would greatly reduce the incidence of false positives and false negatives and would provide a way to determine if a true bio-threat exists in minutes.

Other Spectroscopy-Based Methods

Spectroscopic technologies that compete with those previously mentioned including infrared (IR) spectroscopy. IR spectroscopy cannot compete due to the difficulty with strong water absorption in the IR. Consequently the BWA IR spectra can have spurious strong water signals.

Obviously, many modifications and variations of the present invention are possible in light of the above teachings. It is therefore to be understood that, within the scope of the appended claims, the invention may be practiced otherwise than as specifically described.

We claim:

1. A method for investigating the presence of Anthrax (*Bacillus anthracis*) on a substrate, comprising:

a) selecting a first area from the surface of the substrate, the first area sufficiently large to contain a small plurality of Anthrax organisms, then b) selecting a wide field of view within the first area for further investigation, then c) irradiating the wide field of view plus an area surrounding the wide field of view with sufficient energy to photobleach the irradiated area, then d) collecting Raman shifted light from the wide field of view, then e) analyzing the Raman shifted light for patterns characteristic of Anthrax microorganisms.

2. The method of claim 1, further comprising repeating steps a) to e) for a second area.

3. The method of claim 1, where the step of analyzing includes analyzing the strain of the Anthrax microorganisms.

4. The method of claim 1, where the step of analyzing includes analyzing the viability of the Anthrax microorganisms.

5. The method of claim 1, where the step of analyzing includes analyzing the growth medium in which the Anthrax microorganisms has been grown.

6. A method for investigating the presence of pathogenic microorganisms on a substrate, comprising:

a) selecting a first area from the surface of the substrate, the first area sufficiently large to contain a small plurality of pathogenic microorganisms, then b) selecting a wide field of view within the first area for further investigation, then c) irradiating the wide field of view plus an area surrounding the wide field of view with sufficient energy to photobleach the irradiated area, then d) collecting Raman shifted light from the wide field of view, then e) analyzing the Raman shifted light for patterns characteristic of pathogenic microorganisms.

7. The method of claim 6, further comprising repeating steps a) to e) for a second area.

8. The method of claim 6, where the step of analyzing includes analyzing the growth medium in which the pathogenic microorganisms has been grown.

9. The method of claim 6, where the Raman shifted light from the wide field passes thru a spot, line or image focusing type of spectrometer.

10. The method of claim 6, where the pathogenic microorganisms are anthrax spores.

11. The method of claim 6, where the pathogenic microorganisms are protozoa.

12. The method of claim 6, where the pathogenic microorganisms are cryptosporidia microorganisms.

13. The method of claim 6, where the pathogenic microorganisms are *Escherichia coli* microorganisms.

14. The method of claim 6, where the pathogenic microorganisms are *Escherichia coli* 157 microorganisms.

15. The method of claim 6, where the pathogenic microorganisms are Plague (*Yersinia pestis*) microorganisms.

16. The method of claim 6, where the pathogenic microorganisms are Smallpox (variola ajor) microorganisms.

17. The method of claim 6, where the pathogenic microorganisms are Tularemia (*Francisella tularensis*) microorganisms.

18. The method of claim 6, where the pathogenic microorganisms are Brucellosis (*Brucella* species) microorganisms.

19. The method of claim 6, where the pathogenic microorganisms are *Clostridium perfringens* microorganisms.

20. The method of claim 6, where the pathogenic microorganisms are *Salmonella* microorganisms.

21. The method of claim 6, where the pathogenic microorganisms are *Shigella* microorganisms.

22. The method of claim 6, where the pathogenic microorganisms are Glanders (*Burkholderia mallei*) microorganisms.

23. The method of claim 6, where the pathogenic microorganisms are Melioidosis (*Burkholderia pseudomallei*) microorganisms.

24. The method of claim 6, where the pathogenic microorganisms are Psittacosis *Chlamydia psittci*) microorganisms.

25. The method of claim 6, where the pathogenic microorganisms are Q fever *Coxiella burnetii*) microorganisms.

26. The method of claim 6, where the pathogenic microorganisms are Typhus ever (*Rickettsia prowazekii*) microorganisms.

27. The method of claim 6, where the pathogenic microorganisms are *Vibrio cholerae* microorganisms.

28. The method of claim 6, where the pathogenic microorganisms are chosen from the group of filoviruses (such as Ebola and Marburg viruses), naviruses (such as Lassa fever and Machupo viruses) and alphaviruses (such as Venezuelan equine encephalitis, eastern equine encephalitis, and western equine encephalitis).

29. The method of claim 6, where the pathogenic microorganisms are *Giardia* microorganisms.

30. The method of claim 6, where the pathogenic microorganisms are *Candida albicans* microorganisms.

31. The method of claim 6, where the pathogenic microorganisms are *Enterococcus faecalis* microorganisms.

32. The method of claim 6, where the pathogenic microorganisms are *Staphylococcus epidermidis* microorganisms.

33. The method of claim 6, where the pathogenic microorganisms are *Staphylococcus aureus* microorganisms.

34. The method of claim 6, where the pathogenic microorganisms are *Enterobacter aerogenes* microorganisms.

35. The method of claim 6, where the pathogenic microorganisms are *Corynebacterium diphtheriae* microorganisms.

36. The method of claim 6, where the pathogenic microorganisms are *Pseudomonas aeruginosa* microorganisms.

37. The method of claim 6, where the pathogenic microorganisms are *Acinetobacter calcoaceticus* microorganisms.

38. The method of claim 6, where the pathogenic microorganisms are *Klebsiella pneumoniae* microorganisms.

39. The method of claim 6, where the pathogenic microorganisms are *Serratia marcescens* microorganisms.

40. The method of claim 6, where the irradiating light is in the ultraviolet spectral region with wavelength less than 410 nm.

41. The method of claim 6, where the irradiating light is in the visible spectral region with wavelength less than 780 nm and greater than 410 nm.

42. The method of claim 6, where the irradiating light is in the near infrared spectral region with wavelength less than 2500 nm and greater than 780 nm.

43. The method of claim 6, where the step of analyzing includes analyzing the strain of the pathogenic microorganisms.

44. The method of claim 6, where the step of analyzing includes analyzing the viability of the pathogenic microorganisms.

45. The method of claim 6, where miniaturized components are used to enable a handheld detector.

* * * * *